United States Patent
Tarsaud et al.

(10) Patent No.: US 11,185,289 B2
(45) Date of Patent: Nov. 30, 2021

(54) CAPACITIVE SENSOR FOR RESPIRATORY MONITORING

(71) Applicant: Hill-Rom Services, Inc., Batesville, IN (US)

(72) Inventors: Jean-Francois Tarsaud, Nimes (FR); Gilles Camus, Montpellier (FR); Aye Aung, Singapore (SG); Chau Chong Ye, Singapore (SG); Thierry Flocard, Montpellier (FR); Florian Garnero, Castries (FR); Rachid Oulad Slimane, Montpellier (FR); Pierre Deguignet, Aunes (FR); Nicolas Odic, Saint gely du fesc (FR); Yue Wang, Singapore (SG); Suresha Venkataraya, Singapore (SG); Lokesh Bhatt, Karnataka (IN); Bernard Arnaud, Montpellier (FR)

(73) Assignee: Hill-Rom Services, Inc., Batesville, IN (US)

( * ) Notice: Subject to any disclaimer, the term of this patent is extended or adjusted under 35 U.S.C. 154(b) by 1239 days.

(21) Appl. No.: 15/478,829

(22) Filed: Apr. 4, 2017

(65) Prior Publication Data

US 2017/0290548 A1 Oct. 12, 2017

(30) Foreign Application Priority Data

Apr. 11, 2016 (EP) .................................... 16305424

(51) Int. Cl.
*A61B 5/00* (2006.01)
*A47C 27/08* (2006.01)
(Continued)

(52) U.S. Cl.
CPC .......... *A61B 5/6892* (2013.01); *A47C 27/081* (2013.01); *A61B 5/0816* (2013.01);
(Continued)

(58) Field of Classification Search
None
See application file for complete search history.

(56) References Cited

U.S. PATENT DOCUMENTS

| 4,033,332 A | 7/1977 | Hardway, Jr. et al. |
| 4,320,766 A | 3/1982 | Alihanka et al. |
| (Continued) | | |

FOREIGN PATENT DOCUMENTS

| WO | 9101111 | 2/1991 |
| WO | WO2011027942 A1 | 3/2011 |
| (Continued) | | |

OTHER PUBLICATIONS

EP Search Report dated Oct. 6, 2016.

*Primary Examiner* — Daniel L Cerioni
*Assistant Examiner* — Yasmeen S Warsi
(74) *Attorney, Agent, or Firm* — Barnes & Thornburg LLP

(57) ABSTRACT

A system is provided for monitoring a patient on an air support system. The system comprises a capacitive sensor system having a capacitive sensor positioned at the underside of an air filled mattress, and a respiration signal processing module that receives the output of the capacitive sensor system and is configured to monitor patient respiration. Respiration is monitored by: periodically sampling the capacitive sensor system output to obtain measurements of incremental body displacement; analyzing a plurality of the samples to determine one or more values for parameters of patient respiratory rate; and determining when one or more of the parameter values indicate abnormal respiration. A corresponding method and computer program are also provided.

15 Claims, 27 Drawing Sheets

(51) Int. Cl.
*A61B 5/08* (2006.01)
*A61F 5/56* (2006.01)
*A61G 7/05* (2006.01)
*G01D 5/24* (2006.01)

(52) U.S. Cl.
CPC ............ *A61B 5/4818* (2013.01); *A61B 5/725* (2013.01); *A61B 5/7257* (2013.01); *A61B 5/7278* (2013.01); *A61B 5/7282* (2013.01); *A61F 5/56* (2013.01); *A61G 7/05* (2013.01); *G01D 5/2405* (2013.01); *A61B 2562/0247* (2013.01); *A61G 2203/30* (2013.01)

(56) References Cited

U.S. PATENT DOCUMENTS

| | | | |
|---|---|---|---|
| 4,633,237 A | 12/1986 | Tucknott et al. | |
| 5,448,996 A | 9/1995 | Bellin et al. | |
| 5,808,552 A | 9/1998 | Wiley et al. | |
| 6,067,019 A | 5/2000 | Scott | |
| 6,375,621 B1* | 4/2002 | Sullivan | A61B 5/113 600/484 |
| 7,752,926 B2 | 7/2010 | Caminade et al. | |
| 7,849,545 B2 | 12/2010 | Flocard et al. | |
| 8,429,774 B2 | 4/2013 | Tarsaud et al. | |
| 8,478,389 B1 | 7/2013 | Brockway et al. | |
| 8,598,893 B2 | 12/2013 | Camus | |
| 2011/0047709 A1 | 3/2011 | Tarsaud et al. | |
| 2011/0257552 A1* | 10/2011 | Banet | A61B 5/318 600/534 |
| 2011/0263950 A1 | 10/2011 | Larson et al. | |
| 2012/0132211 A1 | 5/2012 | Halperin et al. | |
| 2014/0277822 A1 | 9/2014 | Nunn et al. | |

FOREIGN PATENT DOCUMENTS

| | | |
|---|---|---|
| WO | 2011162138 A1 | 12/2011 |
| WO | 2012114298 A2 | 8/2012 |
| WO | WO2012155157 A1 | 11/2012 |

* cited by examiner

CAPACITIVE SENSOR FOR RESPIRATORY MONITORING

The present application claims priority, under 35 U.S.C. § 119(a), of European Application No. 16305424.0 which was filed Apr. 11, 2016 and which is hereby incorporated by reference herein.

TECHNICAL FIELD

The present disclosure relates to a sensor arrangement for monitoring a patient on an air support system. Particular embodiments employ a sensor used to monitor particular properties of the patient or support system, such as patient positioning and/or air pressure within compartments of the air support system. Particular embodiments of the present disclosure may be best used in hospital or long-care beds.

BACKGROUND

It is well known in medical fields that devices included within a patient's bed can provide non-invasive monitoring of the patient over long time-periods. However there do not exist such devices for all aspects of a patient's status that are convenient for use and cheap to produce, hence few are used commonly and the medical profession is still dependent on external, often bulky and invasive devices to monitor patients.

Many of these devices require regular checking by nurses or caregivers, and therefore, especially during the night, problems can arise due to a lack of continuous observation. This is a particular concern for patients with medical issues that arise during sleep, such as Obstructive Sleep Apnea (OSA).

It has been identified by the American Society of Anesthesiologists (ASA) that the highest mortality rates in patients with OSA occur during sleep hours, especially early morning hours. Present techniques for detecting OSA are complex. They may involve a formal sleep study or polysomnography, including pulse oximetry as well as essential body functions like brain activity (Electroencephalography/EEG), heart rhythm (Electrocardiography/ECG), skeletal muscle activation (Electromyography/EMG) and eye movement (Electrooculography/EOG). During REM rebound sleep, REM-associated hypoxemic episodes can increase threefold. REM sleep causes muscles of the tongue to relax and thus falling back and blocking the airway. The exacerbation of respiratory depression may occur in the postoperative patient as sleep patterns are re-established and REM rebound occurs. Therefore, simpler techniques are desirable to detect OSA and prevent the consequences of REM rebound sleep.

The treatment for OSA is commonly Continuous Positive Airway Pressure (CPAP). This builds on the knowledge that OSA occurs when the upper airway becomes narrow as the muscles relax naturally during sleep. A CPAP machine stops this phenomenon by delivering a stream of compressed air via a hose to a nasal pillow, nose mask, full-face mask, or hybrid, splinting the airway (keeping it open under air pressure) so that unobstructed breathing becomes possible, therefore reducing and/or preventing apneas. However this method of treatment is not well tolerated in the long term and an alternative is highly desired by both patients and caregivers.

Patient repositioning can be an effective alternative treatment for OSA. Devices capable of repositioning a patient for other medical reasons, such as to prevent bed-sores, are known, as described in U.S. Patent Application No. 2011/0047709, however they are not designed to achieve controlled patient turning.

A device is desired that may provide a cheap and reliable detection of OSA related problems, and other disorders that manifest in breathing irregularities.

Motion detectors using capacitive sensors to monitor respiration or heart beat are known but the present inventors have appreciated that such detectors can be intrusive or uncomfortable, and therefore not practical for use during sleep, because they need to be close enough to the body to work efficiently.

International patent application WO 2011/027942 describes a device for detecting apnea using respiratory motion. It is a capacitive sensor to be attached directly to a patient's chest. This direct contact would allow even low sensitivity sensors to be used, but is likely to hinder the comfort of the wearer, particularly during sleep.

U.S. Pat. No. 4,633,237 describes a sensor used to detect the movement of a person on a bed. The sensor is a flat matrix of multiple pressure sensitive capacitor switches to be located on the bed under the patient's torso. The motion to be detected is large changes in the patient's location indicating their approaching exit from the bed. This device, however well placed to minimize patient disturbance, would not be considered to be designed to monitor the subtle changes in motion that arise during respiration.

The concept of combining patient repositioning and other vital sign monitoring is briefly discussed in international patent application WO 2012/155157. The repositioning, however, is minimal, only designed to minimize bed sores. It is not sufficient for patient turning. All vital sign monitoring is external. There is no discussion of combining the two features in a single device, and none of the herein described documents disclose devices capable of doing so.

SUMMARY

The invention is defined in the independent claims to which reference is now directed. Other features are set out in the dependent claims.

Embodiments of the present disclosure provide a sensing system for monitoring a patient on an air support system. The system comprises a capacitive sensor positioned on the underside of an air filled mattress and a signal processing module that receives the output of the capacitive sensor and monitors patient respiration. Patient respiration is monitored by: periodically sampling the capacitive sensor output to determine measurements of incremental body displacements; analyzing the measurements of incremental body displacements to determine one or more values for parameters of patient respiration; and determining when one or more of the parameter values indicate abnormal respiration.

The perceived drawback of locating the sensor on the underside of the mattress is that the overall capacity of such sensors is quite low (for example about 20 nano-Farads) and they are also generally very sensitive to many external factors. This is made worse by the nature of air support systems, which comprise at least one air compartment defining an outer perimeter with a top surface and a bottom surface. An important factor to the development of pressure ulcers is the application of excessive loading onto the soft tissues of the supported body. Thus, protecting soft tissue viability greatly depends on the ability of the support system to immerse and envelop the body placed on its top surface and spread the patient load over a large area, thereby minimizing interface pressure, while preventing the displacement of the body down to the bottom surface. However, this distribution of load reduces the ultimate signal strength detectable at the sensor.

Despite such drawbacks, the inventors have shown that a capacitive sensor is additionally capable of detecting incremental body displacements that may be used to detect and monitor vital signs on an air support system when placed underneath an air-filled mattress. They discovered that in the middle of the noise spectrum, around the main response of known capacitive sensors, the respiratory information is included as well as the patient movements. For example, the external electronics coupled to the sensor can identify when the patient is experiencing REM rebound sleep or apnea due to changes in their vital signs. This information can be used to adjust the patient's position accordingly, or to activate an alarm to notify a healthcare professional.

This was surprising. The expectation was that it would be impossible to extract this information because it would be hidden by noise, for example because the sensor would be too far from the patient, without direct contact to capture the necessary signals. In addition, it was not imagined that the air mattress could transmit the detected information through such minimum contact. In addition, the belief was that there were too many other factors that could interfere such that it would be impossible to differentiate those signals from respiratory rate, such factors including patient movements, electromagnetic field interference, and air mattress pressure change.

Although capacitive sensors are more effective when placed close to the patient, positioning away from the patient, underneath the mattress, is more comfortable for the patient, and is less of a bed sore risk. It also makes it easier for the sensor to conform to all kinds of bed articulation.

The inventors also appreciated that capacitive sensors used for other purposes can, in addition, be used to provide the additional functionality of respiratory rate monitoring. For example, optionally the capacitive sensor is also used for monitoring the characteristics of the patient's morphology and position on the articulated or non-articulated supporting structure of a bed so that the fluid pressure within air compartment(s) of an air support system can be determined and, optionally, automatically adjusted accordingly. The capacitive sensor has sufficient resolution for this purpose, but is designed to be thin and flexible so that it can be positioned under a mattress without being uncomfortable for the patient and can adapt to all kinds of bed articulation.

Embodiments of the present disclosure may employ a sensor having a specific construction, that is positioned under or within an air mattress. The sensor may be a surface or pad type sensor. It is thin and flexible, and so is able to adapt to different beds, and yet is sensitive enough to capture small movements relatively far from the patient, through the air mattress.

Embodiments of the present disclosure also employ software and/or electronics that are able to filter out the noise from respiratory rate information. The association of particular sensor designs with the electronics and/or software makes it possible to consistently detect respiratory rate robustly.

Optionally, the capacitive sensor is positioned in the interior of the mattress or on the exterior of the mattress. For example, the capacitive sensor may be attached to the bottom surface of the outer perimeter of the air filled mattress.

Optionally, the capacitive sensor comprises at least one capacitive cell including a flat condenser comprising at least one layer of a compressible dielectric insulating material interposed between two layers of conductive material.

Optionally, analyzing a plurality of samples comprises determining a periodic variation in the output of the capacitive sensor system using a predetermined number of accumulated samples, and determining the patient respiratory rate based upon the periodic variation. For example, the periodic variation in the output of the capacitive sensor system may be determined using a moving sample window. Determining when one or more of the parameter values indicate abnormal respiration may optionally comprise comparing the patient respiratory rate with an upper and/or lower threshold value, wherein the patient respiratory rate passing beyond the upper and/or lower threshold value indicates abnormal respiration.

Optionally, the respiration signal processing module is configured to ensure stable respiration is occurring before proceeding to determine whether abnormal respiration is occurring. This may be achieved by periodically sampling the capacitive sensor system output to obtain measurements of incremental body displacement and periodically analyzing a plurality of the samples to determine one or more values for parameters of patient respiratory rate until it is determined that the respiratory rate remains within a predetermined range of rates for a predetermined period of time.

Optionally, the system further comprises a pressure signal processing module that receives the output of the capacitive sensor system and is configured to determine the pressure exerted by the patient's body or the penetration of the patient's body into given areas of the mattress. The mattress may comprise a plurality of inflatable cells communicating with inflation elements, and the system may further comprise an electronic control and regulation device connected to the pressure signal processing module. The electronic control and regulation device is configured to control the inflation elements for filling or emptying said plurality of air-filled inflatable cells, respectively. As an example, this may be done in such a way that the internal inflation pressure of the air inside the cells is equal to a set point pressure predetermined relative to the load pressure of the body of a person resting on the mattress measured by said sensor. Optionally, the electronic control and regulation device may be further configured to receive a signal indicating that abnormal respiration has been detected, and to cause the repositioning of the body of a person resting on the mattress by selectively inflating or deflating one or more selected inflatable cells of the plurality of inflatable cells.

Optionally, the system may further comprise one or more band pass filters each having an upper frequency cut-off of 2 Hz or less, and a lower frequency cut-off of 0 Hz or more. Optionally, each of the band pass filters may have an upper frequency cut-off of 1 Hz or less, and a lower frequency cut-off of 0 Hz or more.

Optionally, analyzing a plurality of the samples to determine one or more values for parameters of patient respiratory rate comprises: performing a cycle counting technique, such as peak counting or zero crossing techniques, on the plurality of samples to determine a value indicative of respiratory rate; also performing analysis of the power spectrum of the plurality of samples to determine a frequency corresponding to a value indicative of respiratory rate; and combining the results of the peak counting or zero crossing technique with the results of the analysis of the power spectrum to determine an output value indicative of patient respiratory rate.

Although cycle counting techniques such as zero crossing, applied to a filtered output are capable of returning a value for respiratory rate, it has been appreciated experimentally that this technique is not always robust enough to give a reliable respiratory rate. The inventors determined that a combination of cycle counting with analysis of the power spectrum allows respiratory rate to be determined accurately and reliably.

Optionally, performing a peak counting or zero crossing technique on the plurality of samples to determine a value indicative of respiratory rate comprises: separately applying each of a plurality of band-pass filters to the output of the sensor, or an output derived from the output of the sensor (e.g. digital samples obtained via an ADC), each band pass filter having a different band-width to the other filters; performing a cycle counting technique, such as peak counting or zero crossing techniques, to determine a value indicative of respiratory rate associated with the output of each of the band-pass filters; and selecting one or more of the values indicative of respiratory rate determined from the output associated with the filters for combination with the results of the analysis of the power spectrum.

Optionally, selecting one or more of the values indicative of respiratory rate determined from the output comprises determining, for each of the outputs associated with a band-pass filter, whether the respiratory rate is stable by comparing the output associated with each band pass filter with the output of one or more other filters and determining whether the determined respiratory rate is within a predetermined range of the respiratory rate determined using the one or more other filters. The filters may be ordered according to bandwidth and comparing the output associated with each band pass filter with the output of one or more other filters comprises comparing the output for each filter with that of its neighboring filters.

It was discovered experimentally that different filter bandwidths can give different results for the respiratory rate when cycle counting is applied. The inventors appreciated that a more accurate respiratory rate could be determined by comparing the output of multiple filters to determine which filters are outputting a stable respiratory rate.

Optionally the respiration signal processing module is further configured to: compare the value of each of the values indicative of respiratory rate determined from the output associated with the filters with a predetermined threshold to determine a set of values SRR(n1); for each value that exceeds the threshold, compare (i) the difference between that value and the respiratory rate determined based upon the results of the analysis of the power spectrum with (ii) the difference between the results of the analysis of the power spectrum with the average value of the set of values SRR(n1); and discard one or more values indicative of respiratory rate determined from the output associated with the filters based upon the comparison.

Optionally, where the periodic variation in the output of the capacitive sensor system is determined using a moving sample window, the respiration signal processing module is further configured to: for each sample window, determine the average value of the values indicative of respiratory rate associated with the output of each of the band-pass filters; compare the average value determined for the current window with a value determined based upon the average value of one or more previous windows; where the comparison indicates that the average value of the current window varies from the average value of one or more previous windows, determine whether any of the values indicative of respiratory rate associated with the output of one of the band-pass filters varies by more than a predetermined amount from a value determined based upon the average value of the one or more previous windows, and if so, discard those values indicative of respiratory rate.

Optionally, the respiration signal processing module is further configured to: divide a current sample window into a plurality of segments; determine, for each segment, whether the average signal value of the segment differs from the average signal value of the sample window by more than a predetermined amount; and replace segments for which the average signal value of the segment differs from the average signal value of the sample window by more than a predetermined amount with segments for which this is not true. In addition, the respiration signal processing module may be further configured to determine, for each segment for which the average signal value of the segment differs from the average signal value of the sample window by more than a predetermined amount, whether any sample value, J, within the segment differs from the average signal value of the window by more than a predetermined amount; divide the window into at least two portions, the first portion spanning from the first sample to a sample J, and the second portion spanning from a sample J to the end of the window; and adjust the sample values for the first portion such that the average of the first portion conforms to the average of the second portion.

Optionally, where more than one value indicative of respiratory rate is determined from the output associated with the filters, a single rate can be selected for combination with the results of the power spectrum analysis. This can be achieved by comparing each of the selected respiratory rates determined from the filter outputs with a respiratory rate associated with the results of the power spectrum analysis.

In this manner, even when multiple different stable respiratory rates are determined based upon the cycle counting technique, the most likely candidate for the actual respiratory rate can be selected.

Optionally, performing analysis of the power spectrum of the plurality of samples to determine a frequency corresponding to a value indicative of respiratory rate further comprises determining the N highest peaks within the power spectrum and identifying, from the determined peaks, the peak associated with respiration rate based upon the cycle counting technique.

Where multiple peaks are detected using the power spectrum analysis the most likely candidate peak for actual respiration rate can be selected based upon the complimentary results obtained using cycle crossing techniques. This improves the likelihood of determining an accurate respiration rate.

Optionally, combining the results of the cycle counting technique with the results of the analysis of the power spectrum to determine an output value indicative of patient respiratory rate comprises determining a weighted average of the value determined according to the cycle counting technique and the power spectrum analysis technique. Optionally, historical data from previous samples may also be included in the weighted average.

Optionally the system may further comprise an alarm, the system being configured to activate the alarm when abnormal respiration is determined.

Embodiments of the present disclosure provide a method for monitoring a patient on an air support system, the method comprising: receiving, at a respiration signal processing module, the output of a capacitive sensor system having a capacitive sensor positioned at the underside of an air filled mattress; and at the signal processing module: periodically sampling the capacitive sensor system output to obtain measurements of incremental body displacement; analyzing a plurality of the samples to determine one or more values for parameters of patient respiratory rate; and determining when one or more of the parameter values indicate abnormal respiration.

Embodiments of the present disclosure may also provide a computer program which when executed on a respiration signal processing module causes it to carry out the method of receiving, at the respiration signal processing module, the output of a capacitive sensor system having a capacitive sensor positioned at the underside of an air filled mattress; and at the signal processing module: periodically sampling the capacitive sensor system output to obtain measurements of incremental body displacement; analyzing a plurality of the samples to determine one or more values for parameters of patient respiratory rate; and determining when one or more of the parameter values indicate abnormal respiration.

Any of the optional features described above may be combined with one another, as appropriate. The optional features may also be implemented within the method and computer program for monitoring a patient.

It should also be noted that according to a further aspect one or more of the optional features described above, and in the dependent claims, may also be used in a sensing system for monitoring a patient on any type of support system, not just air. The system comprises a capacitive sensor positioned at any appropriate location (e.g. above or below a mattress, or on the patient themselves) for detecting properties of the patient, and a signal processing module that receives the output of the capacitive sensor and monitors patient respiration. Patient respiration is monitored by: periodically sampling the capacitive sensor output to determine measurements of incremental body displacements; analyzing the measurements of incremental body displacements to determine one or more values for parameters of patient respiration; and determining when one or more of the parameter values indicate abnormal respiration.

BRIEF DESCRIPTION OF THE DRAWINGS

The disclosed embodiments will now be further described by way of example only and with reference to the accompanying figures in which.

DETAILED DESCRIPTION

Figure 1:
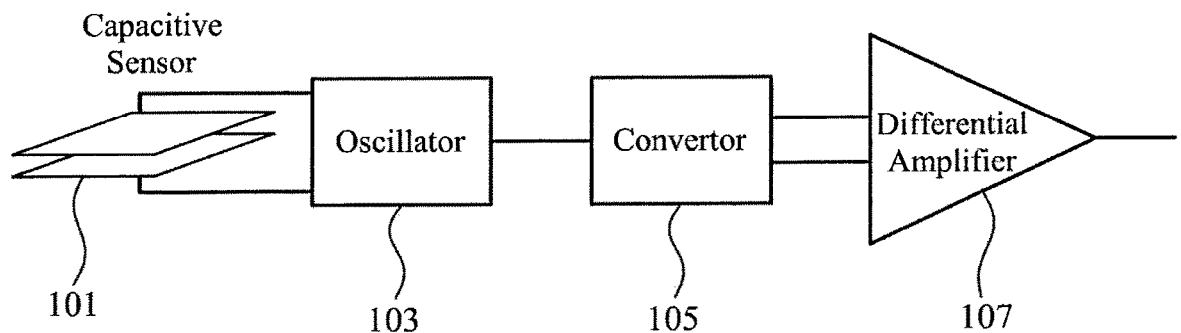
FIG. 1 is an example of a capacitive sensor system for use in embodiments of the present disclosure.

FIG. 1 shows an example of a capacitive sensor system used to detect the characteristics of the patient's morphology and position on an articulated or non-articulated supporting structure of a bed. Such a sensor may be used, for example, to adjust the fluid pressure within the air compartment(s) of an air mattress accordingly. The capacitive sensor system displays sufficient resolution to perform this task.

In order to be appropriately reactive and selective, the capacitive sensor 101 may be connected to an electronic circuit that performs the necessary processing such that the output signal from the electronic circuit of the capacitive sensor is a function of the load applied by the body on the support system. The electronic circuit may, for example, include an oscillator 103, a frequency-voltage convertor 105, and a differential amplifier 107.

The capacitive sensor is placed under the mattress in an air support system and is used primarily to determine whether the air support system should be inflated or deflated. Whether the air support system should be inflated or deflated may be determined by comparison with the signal from one or more pressure transducers, which are used to measure the air pressure within the air compartment(s). The capacitive sensor cooperates with one or more pressure sensors that measure the fluid pressures and the system computes the appropriate pressures to immerse and envelop the patient. Both types of sensor may be used because information from either the capacitive sensor or the pressure sensors alone may not be enough for a closed loop sensing system to operate automatically. The pressure sensor output signals may also be combined with the signal from an accelerometer that is used as a tilt sensor to determine bed back rest angle, since back rest angle also impacts the pressure required to support a patient. This is only an example of the possible ways to determine whether inflation or deflation is required.

The overall capacitive sensor system may be described as the capacitive sensor and the relevant control environment including the electronic circuitry, the pressure transducer(s) and their respective interconnections.

According to one embodiment, the capacitive sensor may be the same type of sensor used within a "ClinActiv+" air mattress replacement system, which herein is used as an example of an air support system. Further examples and details of possible air mattresses with which embodiments of the present disclosure may be used are provided below.

The capacitive sensor may particularly be comprised of one or more flexible sensing pads located on and fixed to the upper surface of the patient support deck, or attached to or integral with the lower surface of the mattress. The sensor may be located at the seat and/or thigh sections of the support deck. Further examples and details of possible sensors with which embodiments of the present disclosure may be used are provided below.

The same capacitive sensor can be used to detect incremental body displacements allowing the detection and monitoring of vital signs. The ability of the sensing system to detect vital signs depends on its operating frequency when the capacitive sensor is connected to the oscillating circuit. Respiration causes potentially detectable movements.

The normal respiration frequency of a patient spans from around 0.1 Hz-0.4 Hz, which corresponds to around 6 to 24 breaths/min and can be correctly detected by the sampling rate of the sensing system of the ClinActiv+ support system.

Figure 2:
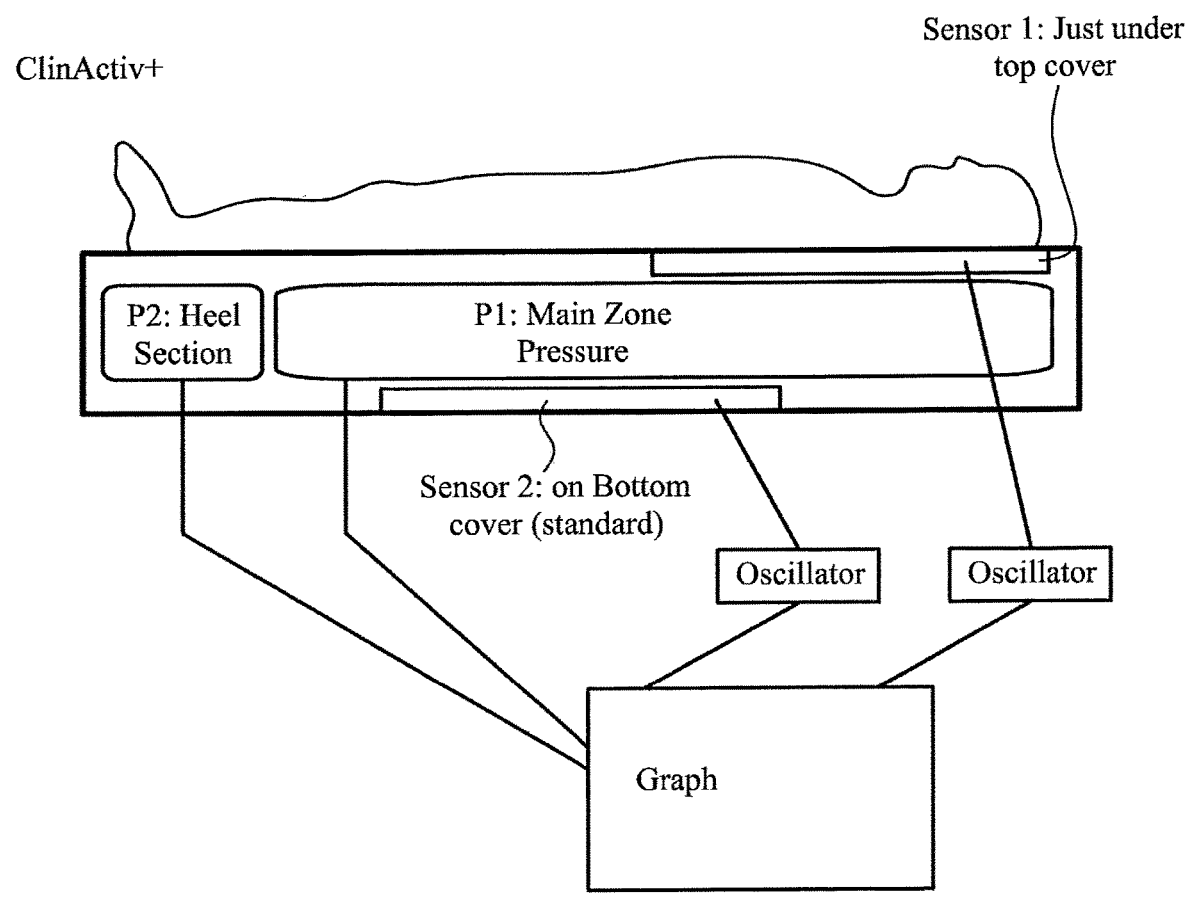
FIG. 2 is a schematic example of an arrangement for using capacitive sensors for respiration monitoring.

Investigations into the feasibility of using such sensors for respiration monitoring were performed using an arrangement as shown in FIG. 2. The apparatus features two capacitive sensors, Sensor1 and Sensor2, for recording and comparison purposes.

The purpose of Sensor1 is to evaluate the efficacy of a capacitive sensor located closer to the chest. It is the control arm for Sensor2.

Sensor2 is a capacitive sensor for regulating the air pressure in the mattress, normally being used in adjusting the fluid pressure within air compartment(s) of an air mattress, for the automatic adjustment of the immersion, envelopment and displacement of the body on the air support system. The sensor may be the same one used in the ClinActiv+ support system, which is very thin and conformable, and is barely noticeable by the subject when positioned under the mattress.

Figure 3:
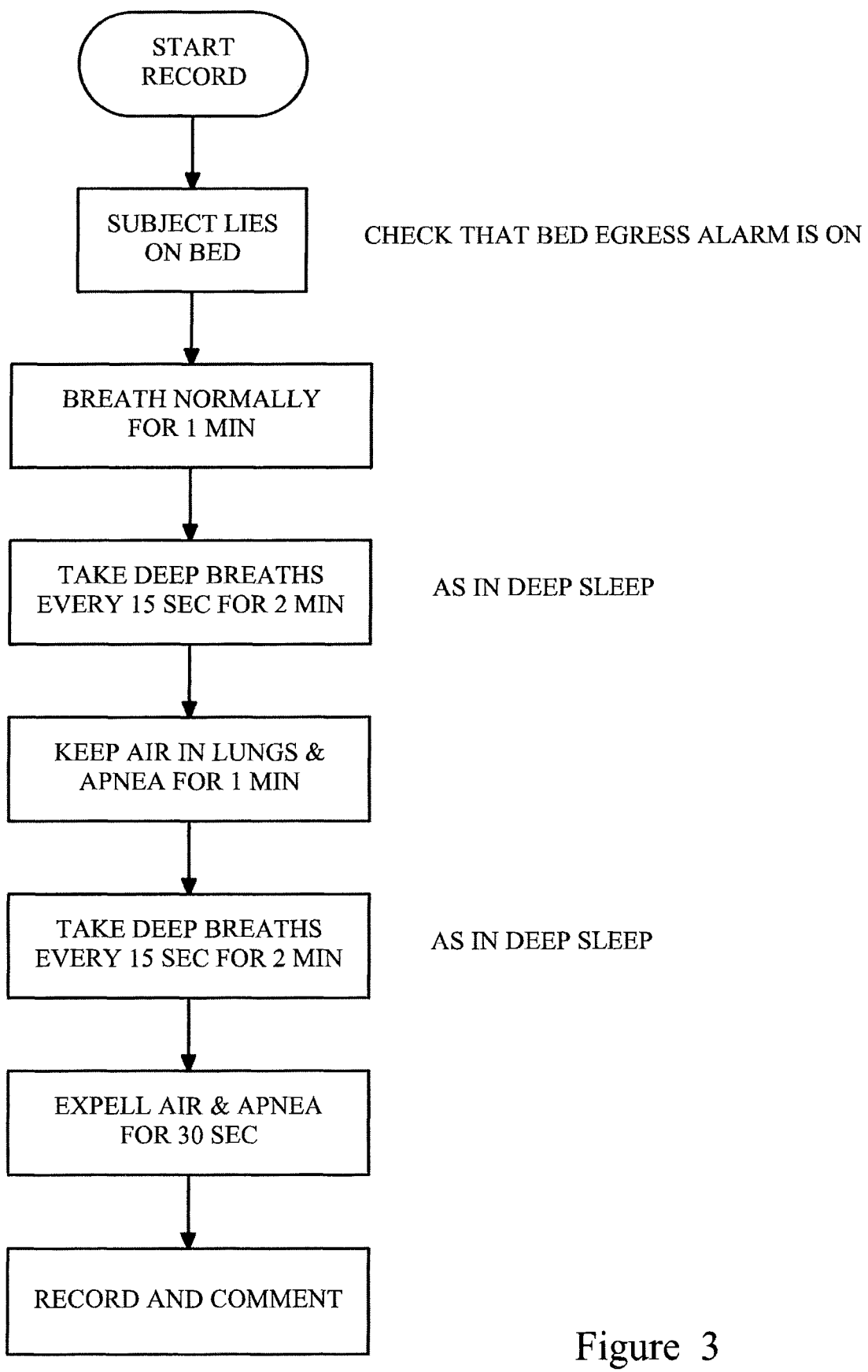
FIG. 3 is an example of a trial script used to test capacitive sensors for respiration monitoring.

Having subjects with various morphologies accommodated on the air support system, the same trial script as shown in FIG. 3 was applied for each sensor. Sensor1 was used for recording only. The purpose of Sensor1 was to check the assumption that a sensor positioned closer to the patient provides more efficient signal capture.

For each of Sensor1 and Sensor2, for different morphologies, the following steps were undertaken, as also illustrated in FIG. 3:

1) Start recording data.
2) Subject lies on the bed. Because the support system (the ClinActiv+) used in the tests includes a bed exit alarm, a check may also be performed at this stage to ensure that the bed exit signal is switched on, although this is an optional aspect depending upon the type of support system used.
3) Let the subject breath normally for 1 minute.
4) The subject takes a deep breath approximately every 15 seconds, as if they were asleep, for 2 minutes.
5) The subject simulates an apnea, with air kept in their lungs for 1 minute.
6) The subject takes a deep breath approximately every 15 seconds, as if they were asleep, for 2 minutes.
7) The subject simulates an apnea by breathing out the air from their lungs and holding for 30 seconds.
8) Capture the data, plot the resulting curves and analyze.

FIGS. 4-8 show the results of testing. In FIGS. 4-8 the upper graph 401 shows the variation in air pressure in the mattress over the duration of the test. In particular, upper line 405 shows the variation in air pressure in the main zone P1 of the arrangement of FIG. 2, whereas the lower line 407 shows the variation in air pressure in the heel zone P2. The lower graph 403 shows the variation in output frequency of the capacitive sensors over the duration of the test.

As can be seen in FIGS. 4-8, the sensing system, and particularly capacitive sensor Sensor2, is able to resolve periodic variations in its output due to patient breathing. This allows detection of breathing irregularities such as apneic episodes where respiratory rate deviates from normal respiratory rate, represented in the graphs by the controlled breath sections. The apnea periods are visually clear and so it is possible, with an appropriate algorithm, to monitor apnea and other breathing irregularities with a capacitive sensor. Surprisingly this is the case regardless of whether the same sensor configured and calibrated for regulating the mattress air pressure is used, or an independent sensor is placed on top of the mattress close to the patient.

Regular respiration, as occurring within a quiet sleep sequence, is normally detected. Also detectable is the breathing pattern including breathing speed and relative amplitude. As a consequence, because of their greater amplitude, deep breaths can be easily captured. As exhibited in FIGS. 4-8, regular as well as irregular respiration patterns are detectable, whatever the patient's morphology and whatever the elevation of the angle of the bed backrest.

Figure 4:
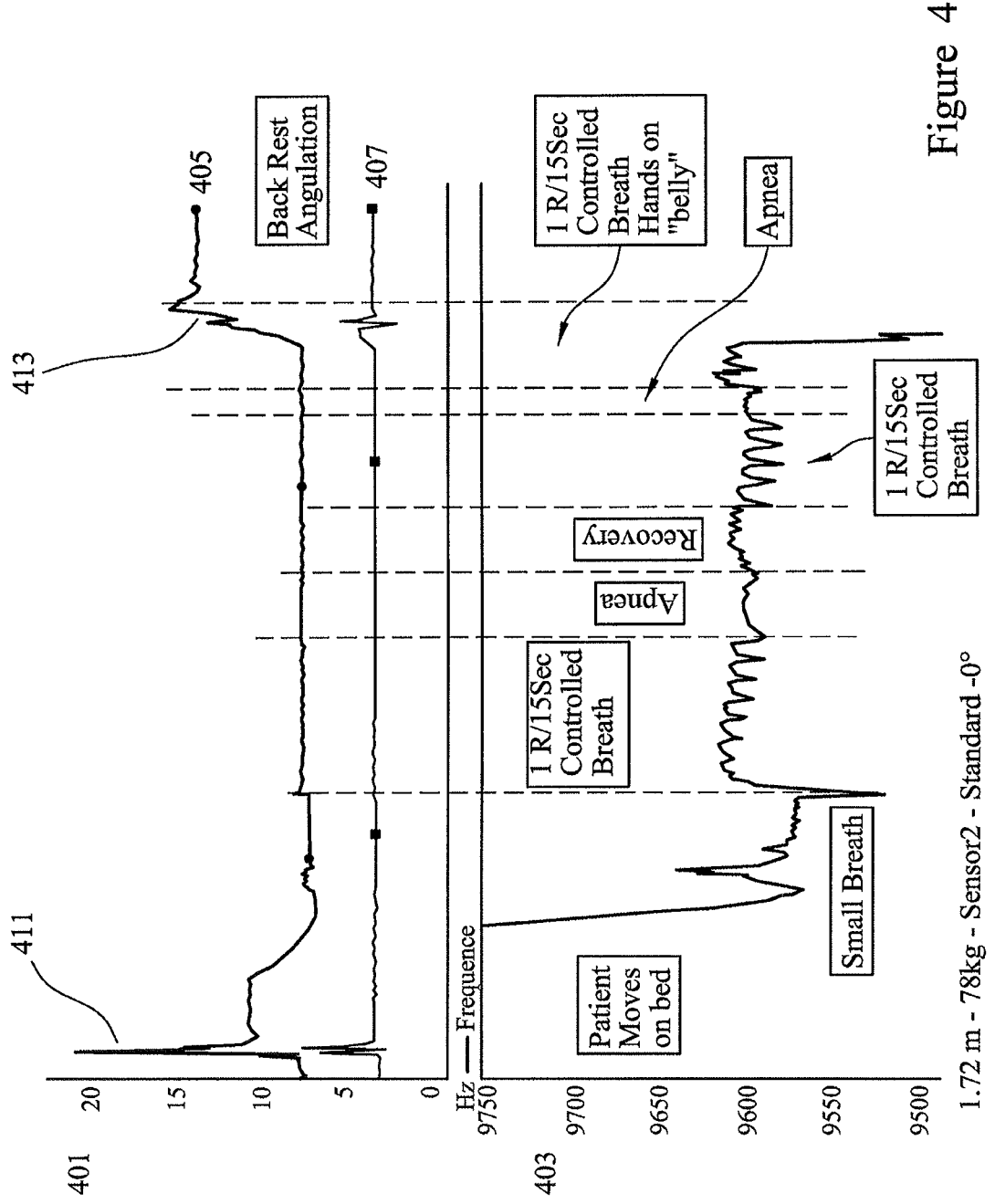
FIGS. 4-8 are graphs showing the results of testing the apparatus for using capacitive sensors for respiration monitoring.
Figure 5:
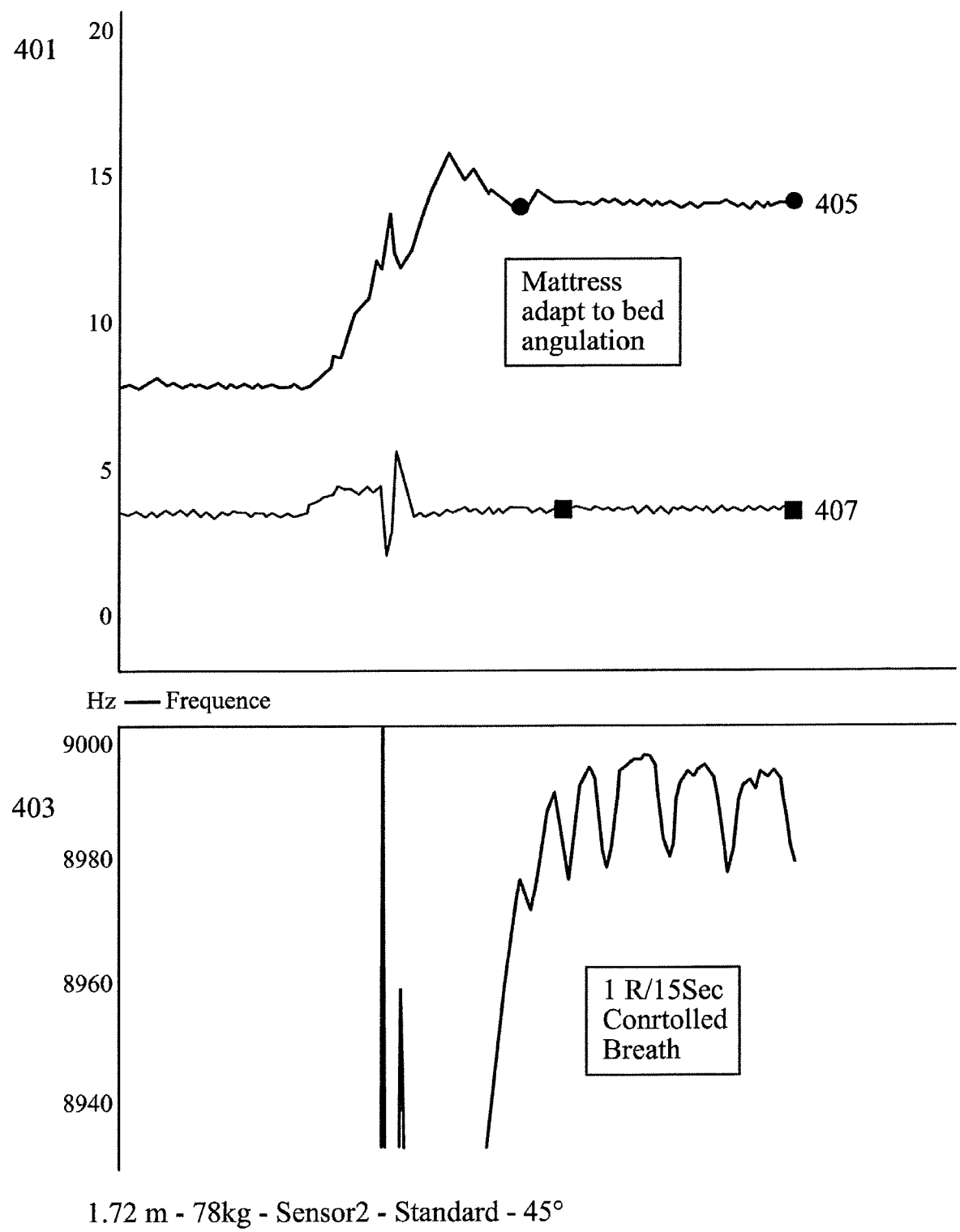
Figure 6:
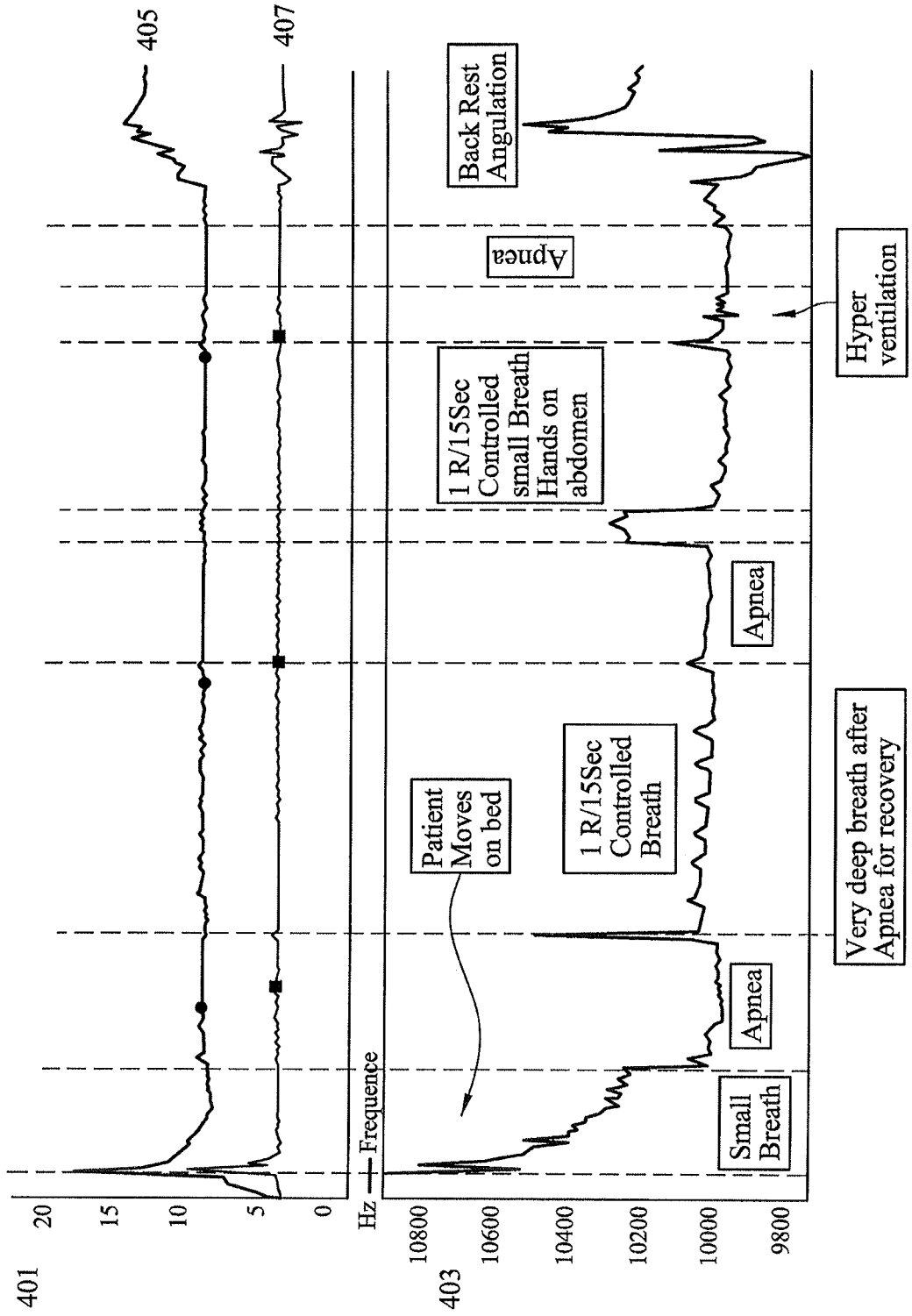
Figure 7:
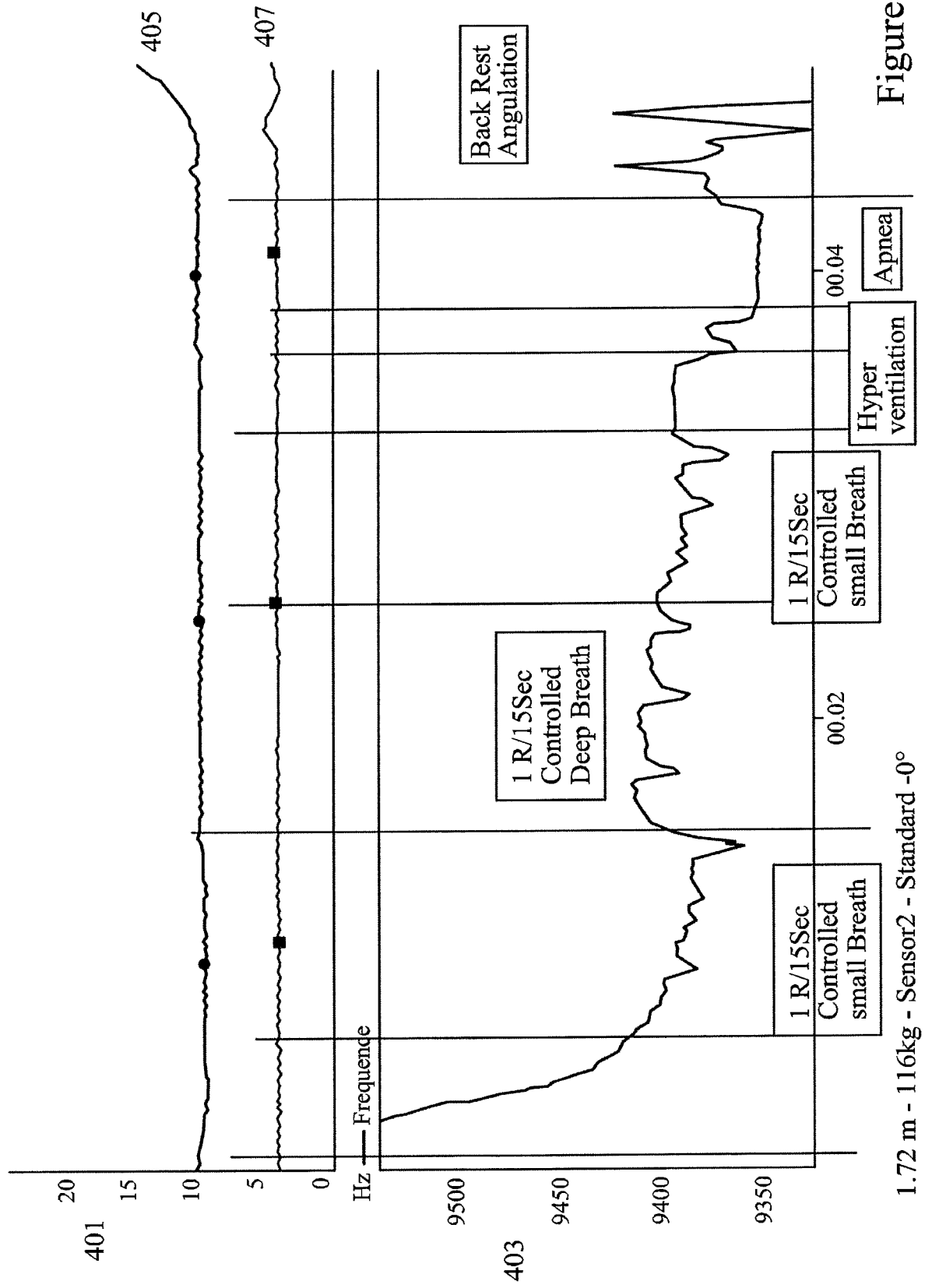
Figure 8:
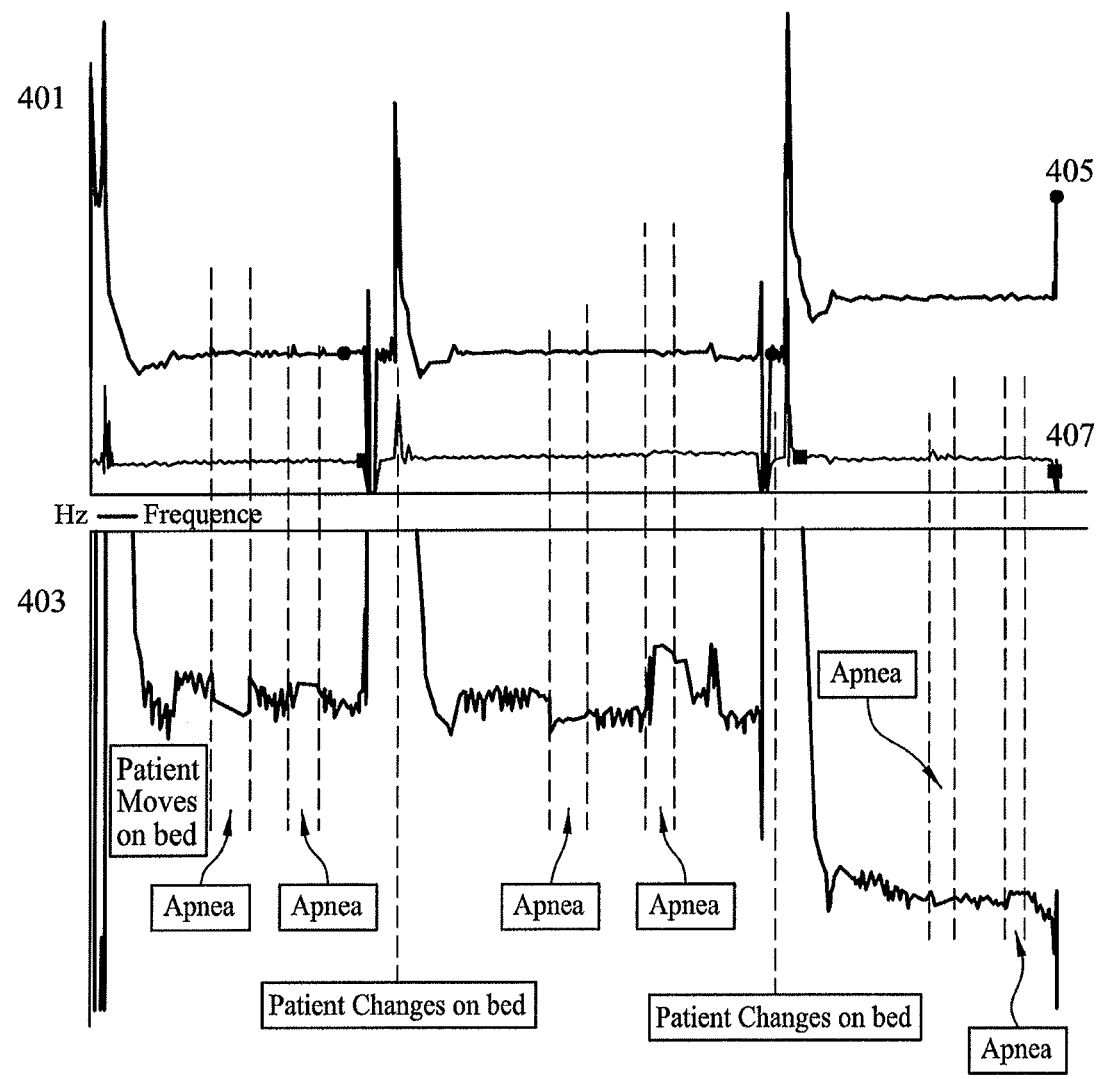

Some points regarding FIGS. 4-8 are of note. In FIG. 4, the spikes in pressure 411 early in the test are caused by the patient getting onto the bed. The pressure increase 413 seen towards the end of the test is caused by an increase in back rest angle, which increases pressure particularly in the main pressure zone P1. FIG. 5 demonstrates that detection of breathing rates is possible regardless of back rest angulation. FIG. 6 confirms that the output of Sensor1 provides a stronger signal, confirming the bias that capacitive sensors should be placed as close to the patient as possible to detect patient properties. FIG. 7 confirms that detection of respiratory rate is possible for heavier patients. FIG. 8, which shows the results of the test for three patients in a row, further confirms that respiration rates can be detected for different morphologies, and particularly different patient mass (the three patients tested in FIG. 8 varied by mass from lightest on the left hand side to heaviest on the right hand side).

Based on this information, histograms and one-to-one comparisons can be set up. The comparisons will be valid whether the recording takes place over some period of time for the same individual or whether two individuals' sleeping patterns are being compared.

It was therefore shown that the same sensor (Sensor2) can be used both for air pressure adjustment within the air compartments of an air support mattress, and for respiration monitoring. It was also proved that respiratory rate can be monitored in various patient positions, with the patient in the supine position, on their left or right hand sides, for varying angles of head of bed elevation, as well as for fast changes of patient's respiratory rate.

Generally the detection method employed will comprise of an initialization stage, a respiratory rate determination stage and a display and/or output stage, where the respiratory rate is output to a display, is used to trigger an alarm, and/or is used to control patient positioning.

Figure 9:
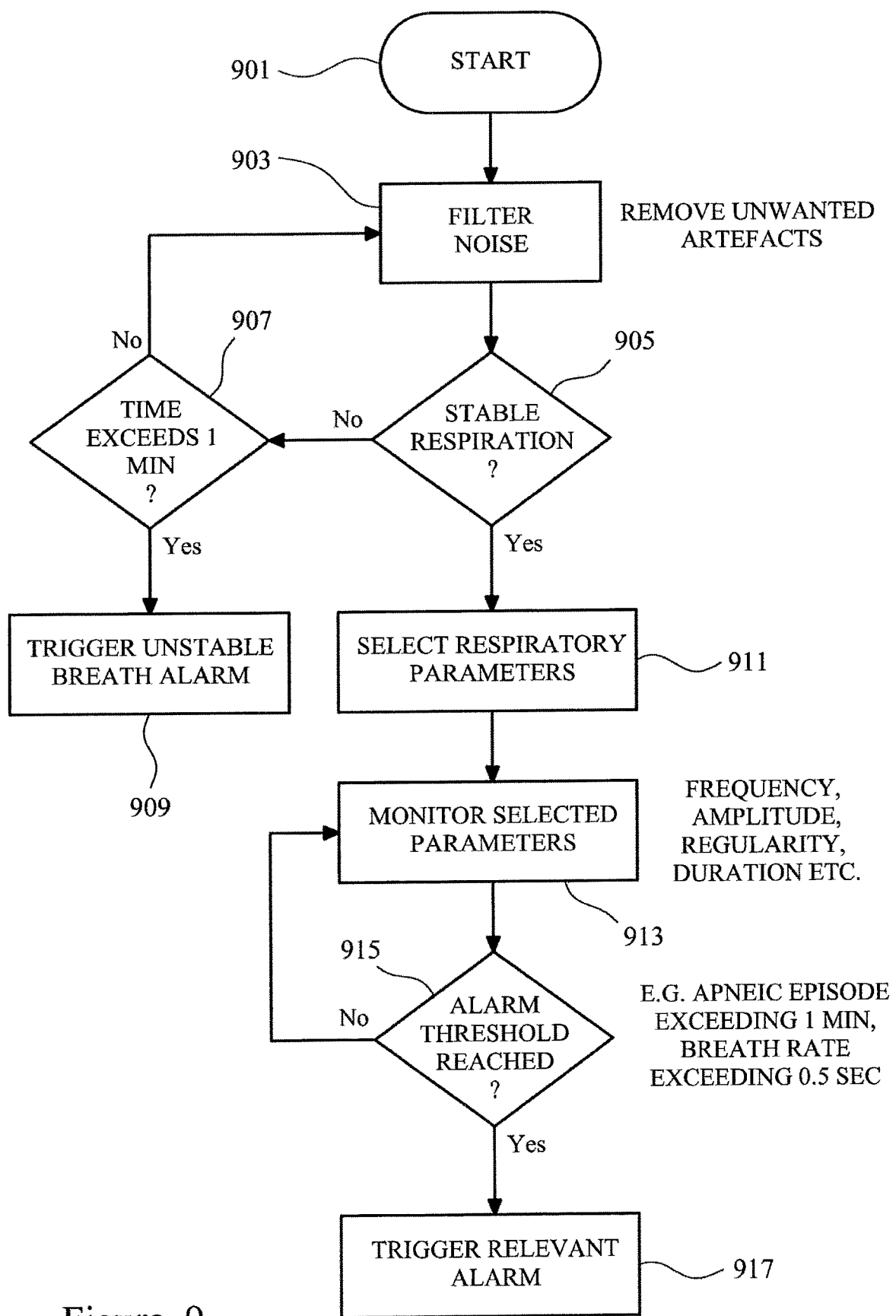
FIG. 9 is an example of a method for processing of the output of the capacitive sensor system to determine one or more values for parameters of patient respiratory rate.

An example of a signal processing algorithm that can be used to monitor patient respiration is described in FIG. 9. Such an algorithm can be applied, by a processing module, to data received from a sensor such as Sensor2 above, being a capacitive sensor positioned at the underside of an air filled mattress.

The algorithm starts at step 901 and may perform a filtering step 903 to remove noise and/or unwanted artifacts. In particular, a band-pass filter may be applied to the sensor output in order to extract the signal component caused by small movements or displacements of the subject's body on the air support system. The band-pass filter allows frequencies commensurate with human breathing rates to pass through for further processing.

The band pass filter may pass frequencies between 0 and 2 Hz, or more specifically between 0 and 1 Hz. Even more specifically, the band pass filter may have a lower cut-off frequency of 0.1 Hz or around 0.1 Hz, and an upper cut-off frequency of 0.8 Hz or around 0.8 Hz. In some examples the lower cut-off frequency may be set as low as 0.05 Hz, depending upon the type of breathing irregularities that are being monitored for.

Although step 903 may be carried out by the algorithm in software, it is also possible to use a hardware based band-pass filter prior to the rest of the algorithm in the signal chain.

At step 905 a determination is made as to whether stable respiration is occurring. During this stage the breath per minute (BPM) value according to the sensor output is monitored and it is determined whether breathing rate is stable. Stable breathing rate may require the breathing rate to be within a predetermined range of BPMs, or within a predetermined number of BPMs from a central value. The range or central value may be determined based upon a calibration stage performed earlier in the process, or separately, for a given patient, or may be based upon pre-existing physiological data determined for various patient groups.

In particular, determining stable breathing rate may involve monitoring BPM over a period T1. If it is determined, at step 907, that stable respiration is not established over the particular time period T1, then an unstable breath alarm may be activated at step 909 indicating to a care-giver that the system has been unable to establish stable respiration. This may be due to the patient not being stationary (e.g. adjusting their position or the back rest angle) or because their breathing is actually not stable. The value of T1 may be, for example, set between 30 and 90 seconds. The value of T2 may, for example, be 1 minute, or approximately 1 minute.

As seen in FIGS. 4-8, deep breaths are more easily detectable than small repeated ones, and quiet sleeping breaths are easier to capture than irregular breaths. As such, a particular application of the system would be during sleeping periods. One application would be to trigger an apnea monitor only once regular breathing is captured by the system when the patient is asleep. As such, the stable respiration determination stage 905 may be used to establish that the patient is asleep before the algorithm moves on to monitoring the selected parameters.

Once stable respiration has been established, the desired respiratory parameters to be monitored can be selected at step 911. Selection may also, or instead, occur earlier in the procedure, such as at the start 901.

The algorithm then enters a monitoring stage during which the one or more selected parameters are monitored. The parameters to be monitored may include one or more of the frequency, amplitude, regularity or duration of breaths.

The parameters are monitored at step 913 to determine 915 whether they reach respective alarm thresholds. This may involve determining when a given parameter exceeds or passes a predetermined upper and/or lower threshold.

The alarm threshold may be a particular lower breathing rate. For example, a breathing rate below 1 BPM may indicate an apneic episode. A breathing rate exceeding one breath every 0.5 seconds may indicate hyperventilation.

Monitoring may also optionally include determining whether a threshold is exceeded or passed for more than a predetermined period of time, such that alarms are not activated when the threshold has been passed only momentarily. For example, the alarm may require that the breathing rate is above or below a particular threshold for a particular period of time, e.g. 1 minute, before activation.

At step 917 an alarm is triggered if the alarm threshold is reached. For example, as mentioned above, alarms can be triggered whenever an apneic episode lasts too long.

With various thresholds being defined, for example based on duration, amplitude, frequency, irregularity etc., differentiated low priority or high priority alarms can be initiated, for instance with respect to REM rebound sleep.

The form of these alarms will depend on the treatment objective: attendance requested, sleep disruption needed etc. The alarm may therefore be an audible and/or visual alarm intended to alert a caregiver. The alarm may also, or instead, be intended to alert or awaken the patient, and may therefore be an audible, visual and/or tactile alarm. For example, in response to the alarm being triggered, the air pressure in the air support system may be changed, such as by deflating one or more of the air compartments.

Further improvement in OSA can be obtained when the non-perioperative patient sleeps in the lateral, prone, or sitting positions rather than the supine position. To minimize post-operative morbidity and mortality due to OSA, the supine position should be avoided when possible during the recovery of patients who are at increased perioperative risk from OSA. Lateral positions, as opposed to supine positions, are recommended as a treatment for sleep apnea, largely because the gravitational component is smaller in the lateral position.

Continuous positive airway pressure (CPAP), the most common treatment for OSA, is not well tolerated in the long term and an alternative is highly desired by both patients and caregivers.

The capacitive sensor, which may be used within the sensor system for patient repositioning, can also be used to achieve controlled patient turning, particularly when the system detects an apneic episode. As such, patient turning can be initiated by inflating and/or deflating a particular set of air compartments in the air support system upon the relevant alarm threshold being reached. Such patient turning can be implemented as well as, or instead of, activating an alarm.

This patient turning can be achieved in addition to, and at the same time as, adjusting air pressure in the air support system to deliver uninterrupted therapy to the patient. As such, the sensing system as a whole can be considered as a help to assist in global oxygen supply, both respiratory and circulatory.

An example of a system and technique for performing patient repositioning is described in U.S. Pat. No. 8,429,774, and provides a non-disruptive solution for OSA. The capacitive sensor used in embodiments of the present disclosure may be the same sensor used in the system described in U.S. Pat. No. 8,429,774, the content of which is hereby incorporated by reference herein and described in more detail below.

Figure 10:
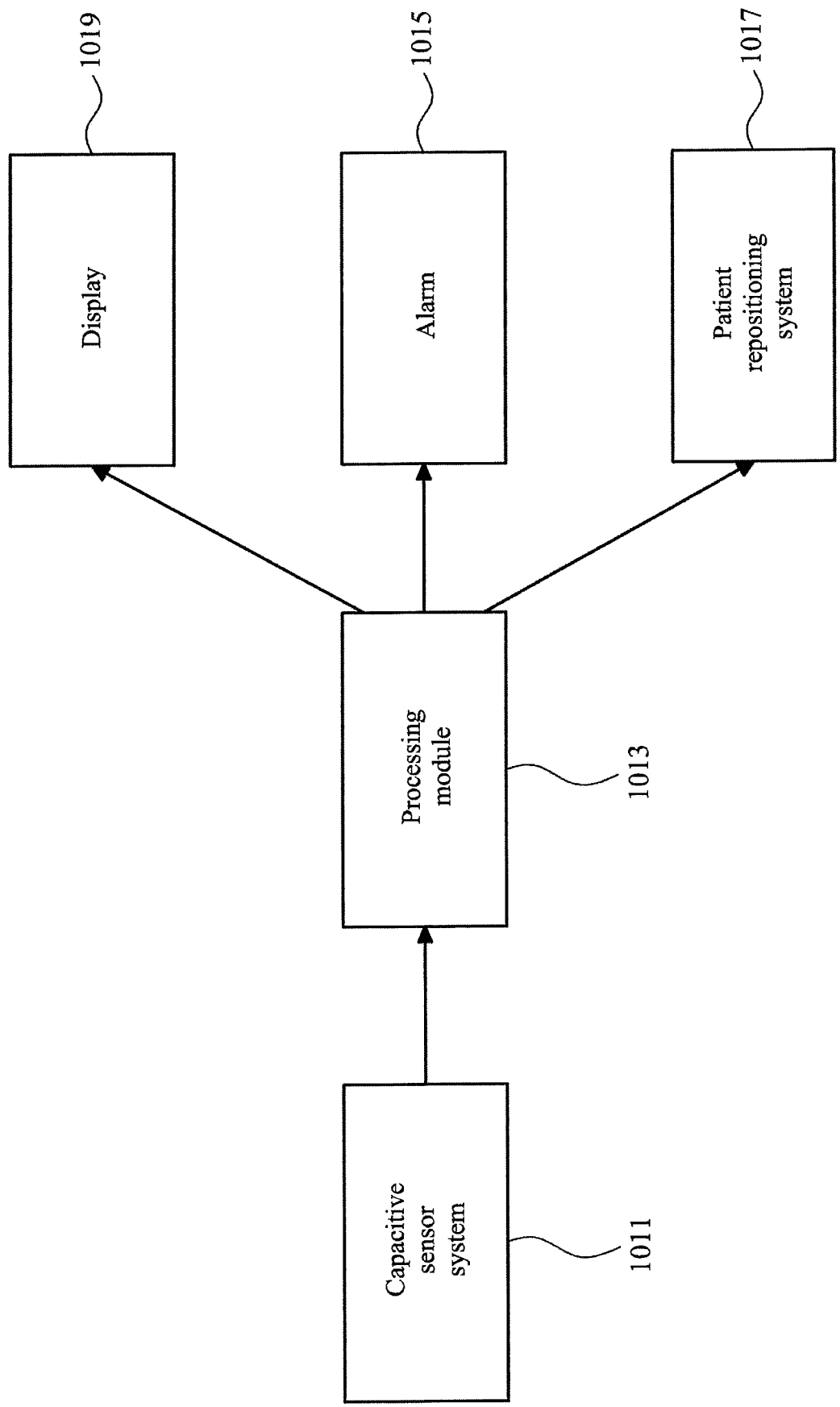
FIG. 10 is an example of the general components used in a system for monitoring a patient on an air support system.

The overall system for monitoring a patient on an air support system will now be described. FIG. 10 shows the general components of such a system. A capacitive sensor system 1011 detects variations in patient load that include variations due to respiratory movements. The output of the capacitive sensor system is passed to a processing module 1013, which performs the processing of the output of the capacitive sensor system to determine one or more values for parameters of patient respiratory rate. The one or more parameters (such as BPM) may be output for presentation to caregivers, or used by the system to determine when one or more of the parameter values indicate abnormal respiration, or both. This may be according to the method described in relation to FIG. 9, or any other method described herein.

Upon determining that abnormal respiration is occurring, an output is triggered. The output may take the form or one or more alarms 1015, triggered to alert a caregiver to abnormal respiration. In addition, or as an alternative, an output may be provided to a patient repositioning system 1017, upon determining that abnormal respiration is occurring, to adjust patient position. In addition, or as an alternative, the determined respiration rate may be presented on a display 1019 proximate to the patient.

Figure 11:
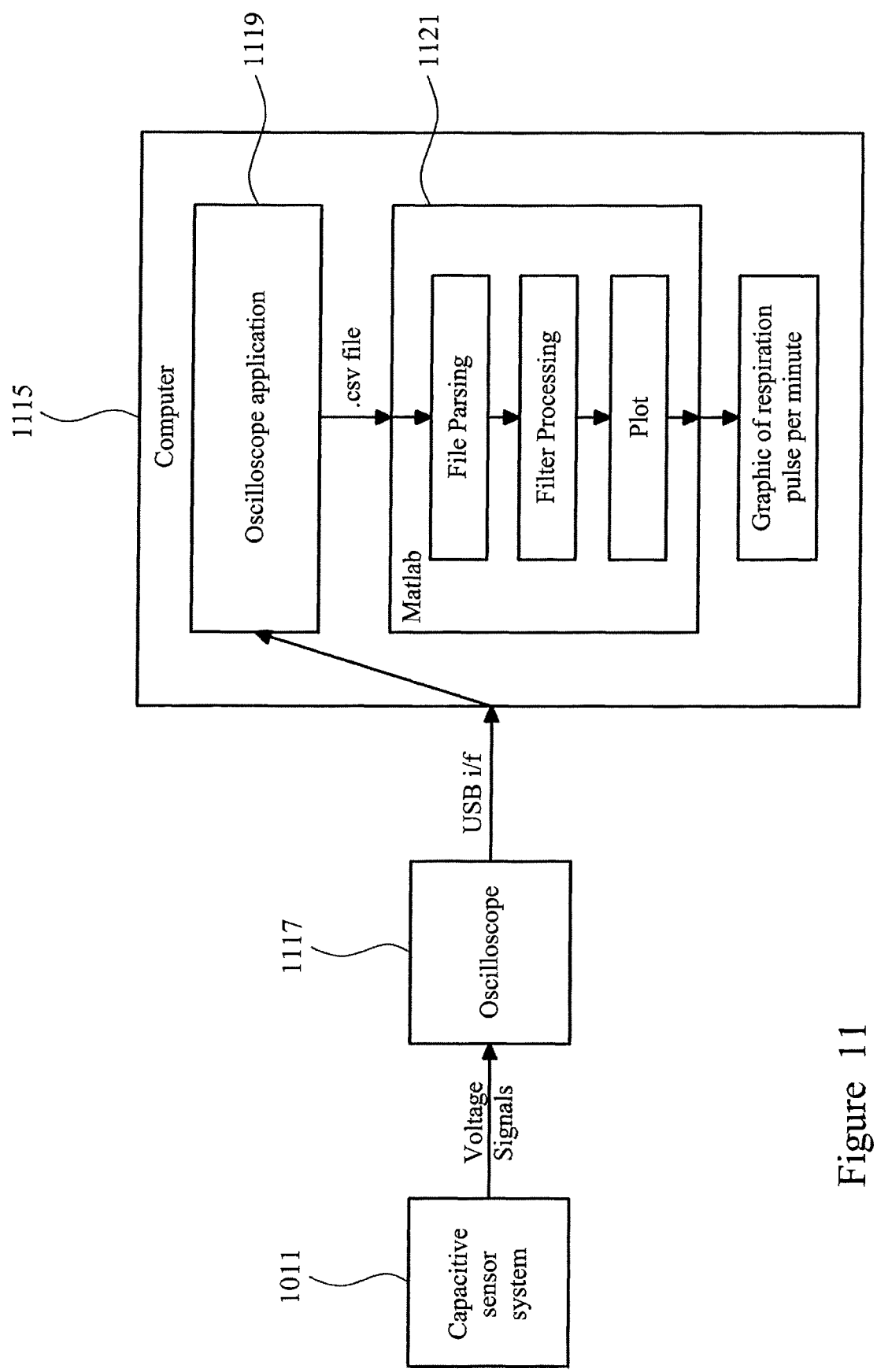
FIG. 11 is an example of the components used in a system for monitoring a patient on an air support system.

FIG. 11 shows an example in which the processing module is in the form of a signal measuring device coupled to a processing means such as a computer. A capacitive sensor system 1011 output is captured by the signal measuring device, such as an oscilloscope 1117. The oscilloscope has a computer interface, such as a USB interface, that allows its signal output to be passed to a computer 1115 for further processing. An example of a suitable oscilloscope would be a PICOSCOPE™ PC Oscilloscope.

The raw data may be processed by appropriate software executing on the computer, such as application 1119. For example, the application is the accompanying PICOSCOPE™ software application, which determines the voltage signals generated by the sensor. The data may be stored in any suitable format to produce an appropriate file containing data indicative of the oscilloscope output, for example a ".csv" file. This file can be passed to an appropriate computing software application such as MATLAB, where the file is parsed to variables and the resulting data is processed through an appropriate filter of the sort described above. For example, the filter may be designed for 0.1 to 0.8 Hz. The resulting data is then processed by the computer in accordance with the monitoring algorithm of FIG. 9, or any other appropriate method described herein, to provide a respiratory monitoring system. As shown in FIG. 11, it is also possible to provide a graphical representation of the respiratory parameters, such as pulse per minute, for review by a user.

Whilst the example of FIG. 11 can provide a working system, for practical implementations it is advantageous to provide a dedicated hardware system.

Figure 12:
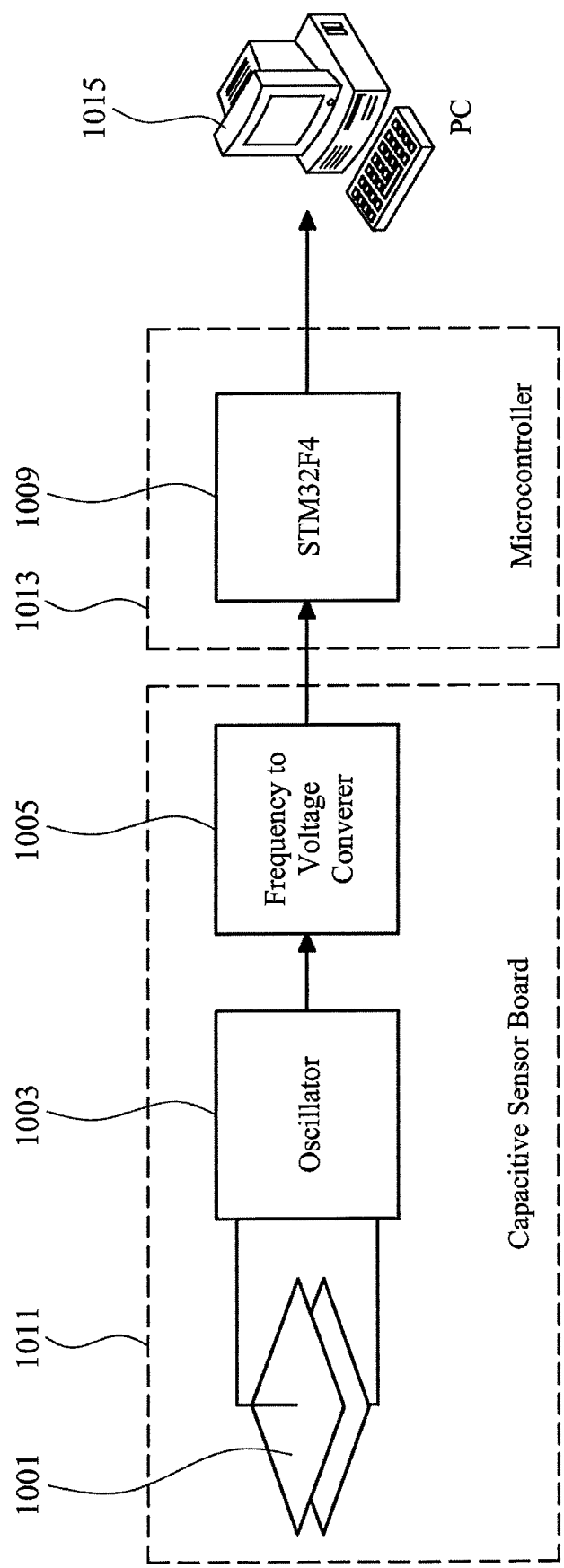
FIG. 12 is an example of the components used in a system for monitoring a patient on an air support system.

FIG. 12 shows an example of such a monitoring system, which comprises a capacitive sensor system 1011 and a processing module 1013 which comprises a microcontroller 1009. As can be seen, in this example the monitoring hardware is divided into two sections, the capacitive sensor system 1011 and a microcontroller 1009. A computer 1015, or other processing means, may also be provided. In some embodiments the processor or computer 1015 forms part of the processing module, sharing the monitoring processing functions with the microcontroller 1009. In some embodiments the computer provides alarm outputs and/or patient repositioning control. It will be appreciated that it is also possible that the computer 1015 or the microcontroller could perform both the processing and the output tasks these types of task, or these tasks could be shared between them in any appropriate way.

The capacitive sensor system 1011, which may be in the form of a sensor board, may comprise a capacitive sensor 1001, an oscillator 1003 and a frequency to voltage converter 1005. As with the sensor of FIG. 1, a differential amplifier (not shown) may also be used.

The capacitive sensor system 1011 outputs a voltage signal varying according to the respiratory movement of a patient on the air support system. The voltage signal from the capacitive sensor system is fed to the microcontroller 1013 for further filtering, if required, and processing to produce measurements of respiration such as respiratory pulse.

Generally, the embodiments described herein use a frequency to voltage converted signal which is then processed as described, since capacitive sensor systems and boards generally include a frequency to voltage convertor (as shown in FIG. 1 for example). However, it is also possible to extract the sensor output directly from the oscillator associated with the capacitive sensor, and use the frequency varying signal directly, as this can provide more accurate measurements of the variation of the capacitive sensor output. The algorithms described herein are generally applicable to either type of signal, and the hardware can be modified as appropriate, as would be known to the skilled person, depending upon which signal is being used.

Figure 13:
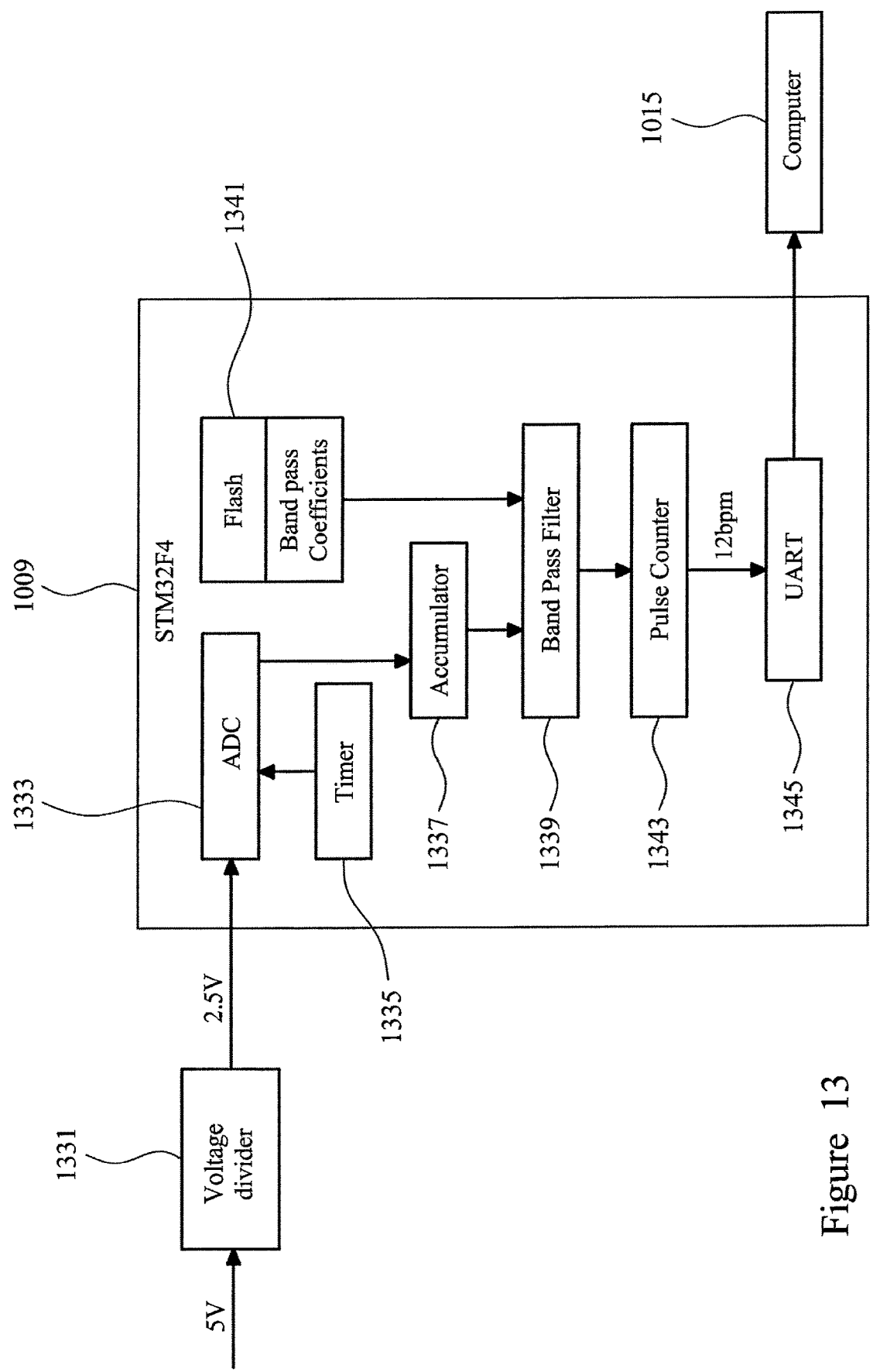
FIG. 13 is a functional schematic of an appropriately configured microcontroller for use in the system of FIG. 12.

FIG. 13 shows a functional schematic of an appropriately configured microcontroller 1009 of FIG. 12 in more detail. In this example the microcontroller is from the STM32F4 series, although other suitable microcontrollers could be used.

The microcontroller 1009 receives the voltage signal from the capacitive sensor system 1011. A voltage divider 1331 may be applied as appropriate to the incoming signal, and example voltages are given in FIG. 13.

The signal is converted to digital by analogue to digital converter 1333. A suitable timer 1335 sets the ADC sample rate. The ADC may sample the data at a rate of N samples per second, for example 1 K samples per second.

An accumulator 1337 accumulates a predetermined number, M×N, of samples and then provides them to a band-pass filter 1339. For example, M may be 30 so that the accumulator accumulates 30K samples before feeding these to the band pass filter.

The band pass filter parameters may be stored in flash memory 1341. The parameters may be predetermined based on calibration or test data, for example they may be the MATLAB coefficients determined during testing using the system of FIG. 11.

A pulse counter 1343 processes the filtered data to determine a respiration parameter, which in this example is a value indicative of the number of breaths per minute (BPM) of the patient. The pulse counter may determine the BPM value according to a process described below.

Once calculated, the respiration parameter is output to a computer 1015, or other processing device, for monitoring. The data may be output via serial communication, using a Universal Asynchronous Receiver/Transmitter (UART) 1345 for example. The monitoring is performed in accordance with any appropriate method described herein, such as the method of FIG. 9.

The calculation may be performed continuously using a moving window of samples on a FIFO basis. Every period of time, a new set of N samples are appended to the M×N samples in the accumulator, with the earliest set of N samples being discarded. For example, every second a new set of 1K samples are appended to the 30K sample buffer held by the accumulator, effectively applying a moving window. This allows a real time respiration count to be achieved.

Figure 14:
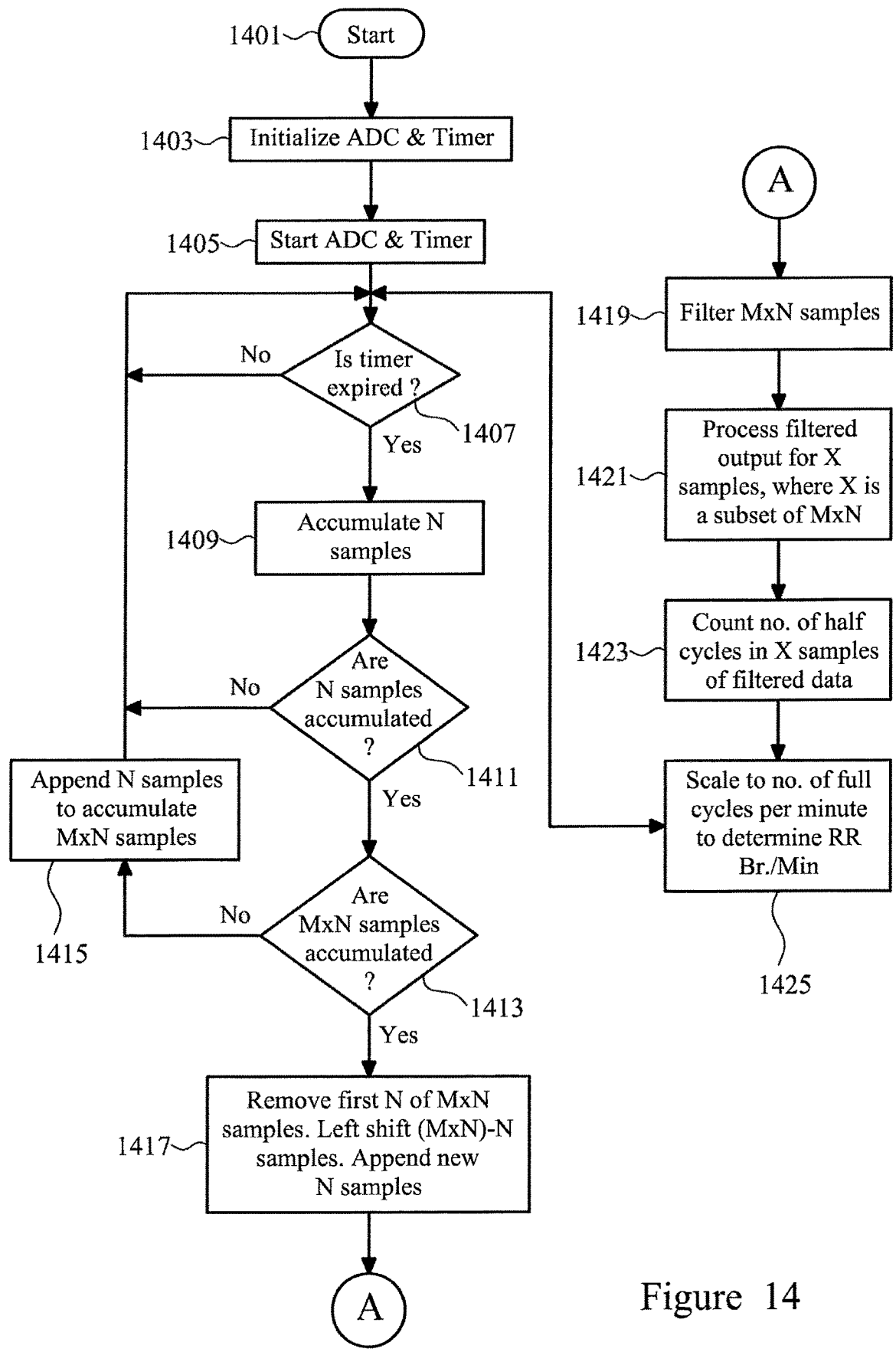
FIG. 14 is an example of an algorithm detailing how a real time respiration count can be determined.

FIG. 14 shows an example of an algorithm detailing how a real time respiration count can be determined using a rolling sampling window. This algorithm can be used in any embodiments of the present disclosure.

The algorithm starts at step 1401. If necessary, the ADC and clock are initialized and started at steps 1403 and 1405 respectively. As an example, the timer may be set to 10 msec, with the ADC collecting 1K samples per second.

Sets of N samples are accumulated and appended to one another until a set of samples of the desired size M×N is accumulated, where N is greater than M and M is indicative of the period of time over which respiratory rate is to be determined on a rolling basis. It should be a long enough period of time to ensure a stable measurement of respiratory rate, so that minor variations in respiratory rate over the period do not cause unnecessary fluctuations in the determined rate. As an example, N may be 1,000 samples, and M×N may be 30,000 samples. This means that at a sample rate of 1,000 samples per second, M represents a rolling window of 30 seconds of samples, such that respiratory rate will be determined for a period of 30 seconds worth of samples.

In the example of FIG. 14, a check 1411 is performed to determine if N samples have been accumulated, and a check 1413 is performed to determine when M×N samples have been accumulated. When M×N samples have been accumulated the samples are ready to be processed to determine respiratory rate.

At step 1417, in order to effect the rolling sampling window, the first N of the M×N samples (i.e. the earliest received of the M×N samples) are removed from the accumulated samples, which are shifted along, and the next set of N samples received are appended. This is applied on a rolling basis so that the M×N window is updated every time N samples are accumulated, with the respiratory rate being calculated periodically as the M×N window is updated with new samples.

For each collection of M×N samples the process of determining a respiratory rate is performed. An example of this process is identified following on from point "A" in FIG. 14.

At step 1419 the samples are filtered by filter 1339 as previously discussed herein. The samples are then processed at step 1421 using a signal processing technique, for example zero crossing, to determine a recurring feature of the signal indicative of the number of cycles within the samples. The number of half cycles of the signal within the number of samples can then be determined based upon counting the recurring feature, e.g. the number of zero crossings, at step 1423. The number can then be scaled to the full number of cycles per minute to give a respiratory rate.

Optionally the number of samples that are processed at step 1421 may be a subset X of the M×N samples. For example half of the samples may be processed and the results scaled up to determine the respiratory rate. As a specific example, where N is 1K and M is 30, X may be the 15K to 30K samples accumulated. As such, an additional step may be included in which the number of half cycles is scaled accordingly, multiplying the number of half cycles by 4 and then dividing by 2 in this case to arrive at a value for the number of breaths per minute.

A further example of an algorithm for calculating respiratory rate will now be described. The algorithm shares features in common with the previously described algorithm, and aspects of the algorithms described herein may be combined.

Figure 15:
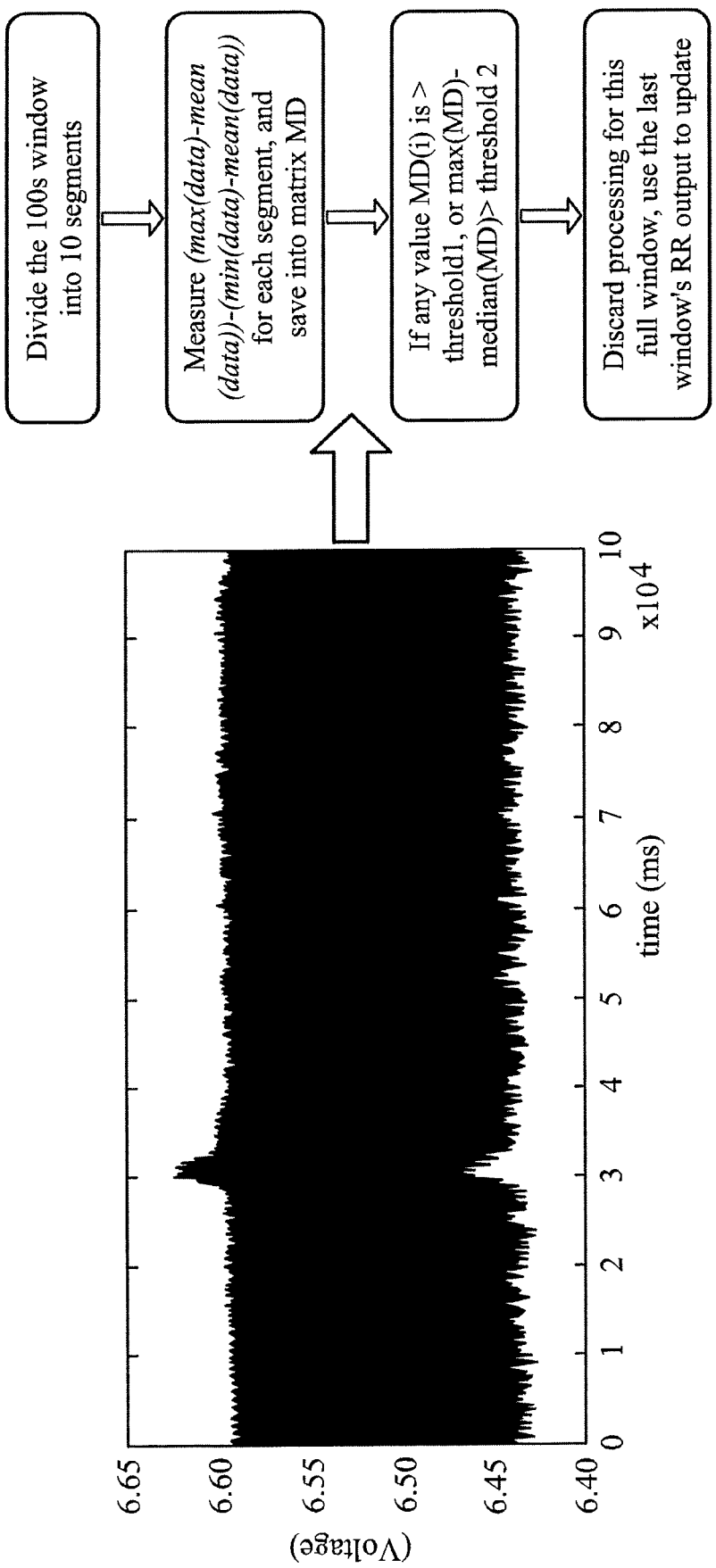
FIG. 15 is an example of a preliminary stage prior to monitoring respiration rate.

FIG. 15 shows an optional preliminary stage. During this stage it is determined whether the patient is in the correct position to begin initialization of respiratory rate monitoring. In particular general motion or movement of the patient's body is detected and samples collected during positioning, or repositioning, can be discarded and will not be used to update respiration rate measurements. Whether samples are discarded or not can be determined based upon the spread of the sample values for a given subset, or segment, of samples. If the data spread for a given segment exceeds a threshold value then the segment is discarded. This optional stage can actually be performed continuously if necessary, so that samples obtained during patient repositioning are ignored from the calculation of BPM.

A given sampling window of A seconds for the output of the capacitive sensor is divided into a subset of segments B. A measurement is taken of the maximum sensor data output, the minimum sensor data output and a determination of the average (e.g. mean) sensor data output for the window is also made. A value, for each segment, is then determined according to:

$$MD=(\max(data)-\text{average}(data))-(\min(data)-\text{average}(data))$$

This value is recorded. If it is determined that the MD value for any segment is greater than a given threshold, threshold1, and/or it is determined that max(MD)−median(MD)>threshold2 (where max(MD) is the maximum MD value for all the segments, median(MD) is the median value for all the segments, and threshold2 is a second threshold value), then the entire window is discarded since it is likely that the patient is still adjusting their position on the mattress. This preliminary or motion detection stage may be performed continuously during operation so that only window samples in which the patient is not repositioning themselves are used to determine and update respiration rate.

An initialization stage may again be used to determine when a stable respiration rate has been established, followed by a monitoring stage in which the respiratory rate is monitored and updated.

During implementation several issues were discovered with initialization and monitoring. The signal to noise ratio varies between subjects and other conditions such as patient position on the support mattress. Determining BPM by counting pulses using peak counting, zero crossing or other techniques for detecting repeating features also gives different results depending upon the filter used, and particularly depending upon the band-pass range of the filter. As such, it was appreciated experimentally that zero crossing techniques (or similar) alone are not always capable for determining respiration rate as robustly as desired. In addition, it was found experimentally that determining BPM using power spectrum analysis techniques is also not as robust as desired. Whilst the FFT power spectrum of the filtered sensor output shows sparse dominant peaks, the most dominant peak does not always correspond to the actual respiratory rate.

Figure 16:
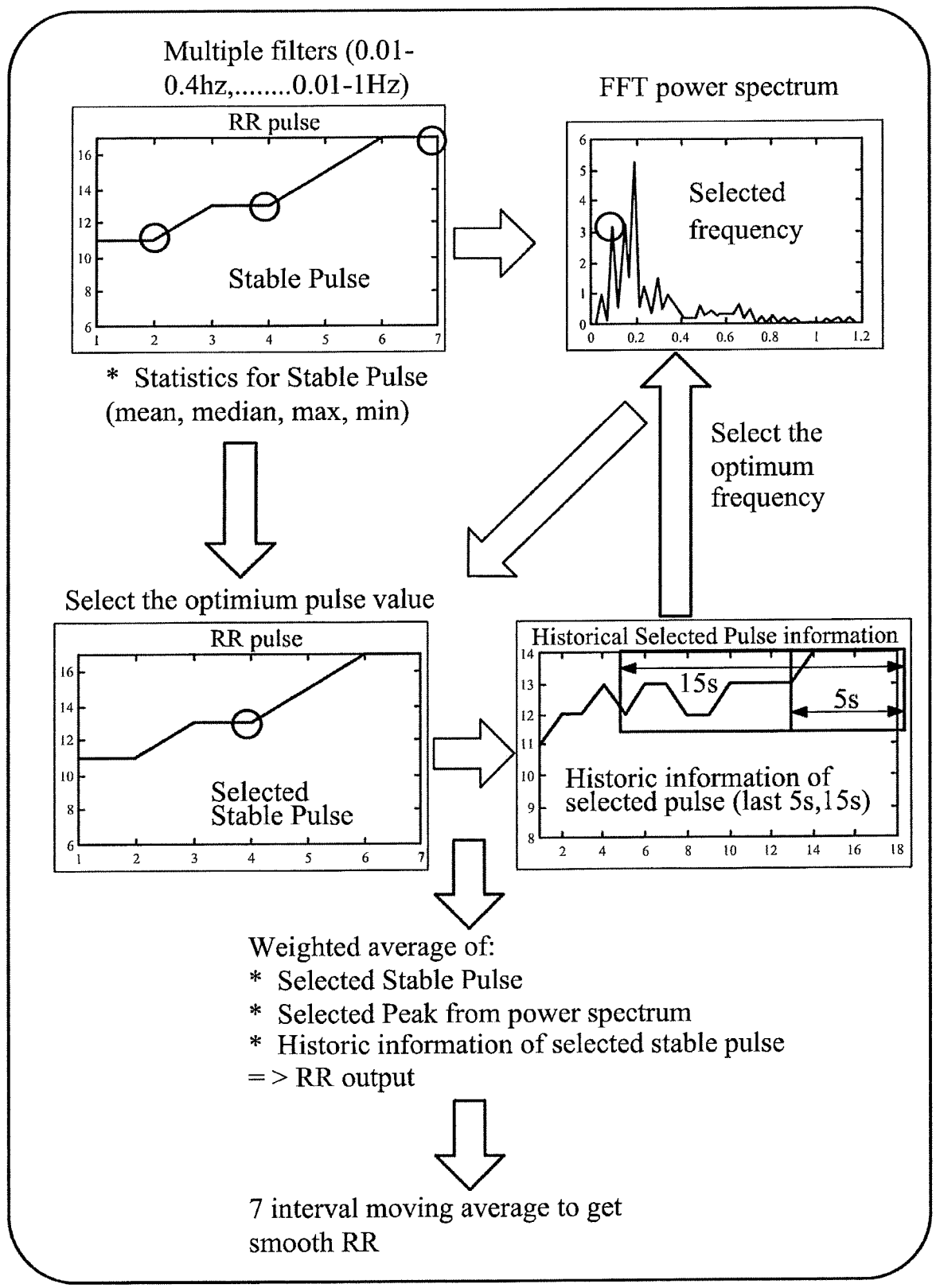
FIG. 16 is an example of a method for determining respiratory rate output by combining two different data analysis techniques.

Embodiments of the present disclosure may therefore use a combination of repeated feature spotting techniques, such as peak counting and/or zero crossing, and power-spectrum techniques, such as power spectrum analysis via Fourier transform, to determine respiration rate for a given sample window. An example of this combination of techniques is shown in FIG. 16. Such techniques may also be applied generally to non-air mattress embodiments as well as air mattress embodiments, and regardless of the location of the capacitive sensor relative to the patient (e.g. the sensor may be on top of the mattress or in any other suitable position).

Zero crossing, or similar cycle counting techniques, may be applied to the sensor output sample window, with multiple different filters applied to determine stable respiration rates for each of the different filters. The optimal stable pulse value can then be selected from the various different rates determined for the various filters. The optimal stable pulse can be determined based upon the stable pulse rates for each of the different filters, optionally taking into account the historical statistics for the stable pulse, including one or more of mean, median, maximum and minimum values for the stable pulse for example.

Figure 17:
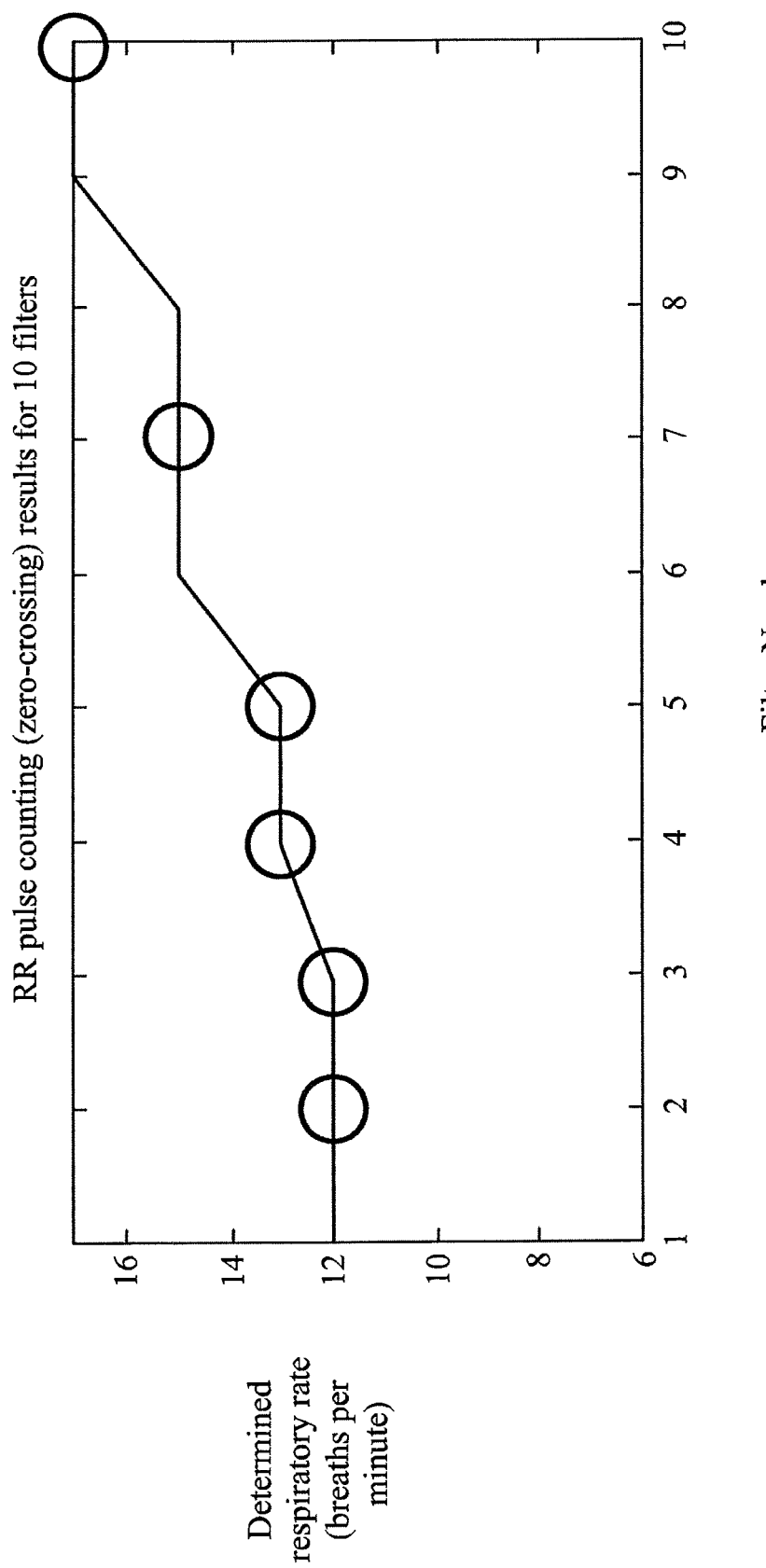
FIG. 17 is an example of identified stable respiration rates determined according to zero crossing techniques.

FIG. 17 shows the results of applying zero crossing techniques for multiple filters applied to the sensor output. As can be seen, different filter numbers produce different results for the determined respiratory rate. The different filter numbers have different bandwidths to one another, with the bandwidths extending between ranges from 0.1 Hz and 1 Hz, for example. It will be understood that different bandwidths may mean the same bandwidth range, but with different lower and/or upper cut-off frequencies, and/or different bandwidth ranges. The example from which the data of FIG. 18 derives uses 10 filters with the following ranges: 0.1-0.4 Hz, 0.1-0.45 Hz, 0.1-0.5 Hz, 0.1-0.55 Hz, 0.1-0.6 Hz, 0.1-0.65 Hz, 0.1-0.7 Hz, 0.1-0.8 Hz, 0.1-0.9 Hz, 0.1-1 Hz.

In some embodiments, the output for respiratory rate for each filter needs to be determined to be stable for it to be used further in the determination of the overall respiratory rate. As an example, the respiratory rate determined for a given filter (i) may be considered stable if the difference in magnitude of respiratory rate for that filter does not differ by a predetermined amount from neighboring filters in the series of filters. The series may be arranged in order of filter band-width range (increasing or decreasing). FIG. 17 shows using circles for the filters for which a stable respiratory rate was determined.

As a specific example, stable RR for the output associated with a given filter in the RR filter array may be assumed where:

absolute($RR(1,i)-RR(1,i+1)$)<1 and absolute($RR(1,i)-RR(1,i-1)$)<1, or, for $i=10$ (i.e. final filter), absolute($RR(1,i)-RR(1,i-1)$)<1

In addition, the power spectrum of the sample window is obtained, for example using Fast Fourier Transform (FFT) techniques. The FFT may be obtained for the output of the sensor with a particular filter applied. In particular, the filter may be the filter with the widest bandwidth used for determining zero crossing based respiration rates. The optimal frequency in the FFT can be determined based upon the identified stable respiration rates for the various filters according to the zero crossing technique and/or historic information for the selected "pulse" (for example the determined BPM rate output by the system) over a given interval, for example an immediately preceding previous period of between 5 seconds and 15 seconds. The optimal frequency corresponds to the respiration rate determined using FFT, and may be further used to select a respiration rate from the stable respiration rates determined using the zero crossing technique as the actual respiration rate output by the system.

Optionally, the overall output respiratory rate may be determined based upon a combination of results for the zero crossing and FFT determined values, and may in particular be determined as a weighted average of a selected stable pulse/respiration rate, selected from the stable pulses determined according to the zero crossing technique, and the pulse/respiration rate corresponding to the selected frequency determined according to the FFT technique. Optionally, the weighted average may also include the historic respiratory rate determined for the currently selected stable pulse (i.e. the pulse associated with the selected filter). A moving average may be obtained over a number of intervals (e.g. 7 intervals) to get a smooth respiratory rate output.

Figure 18:
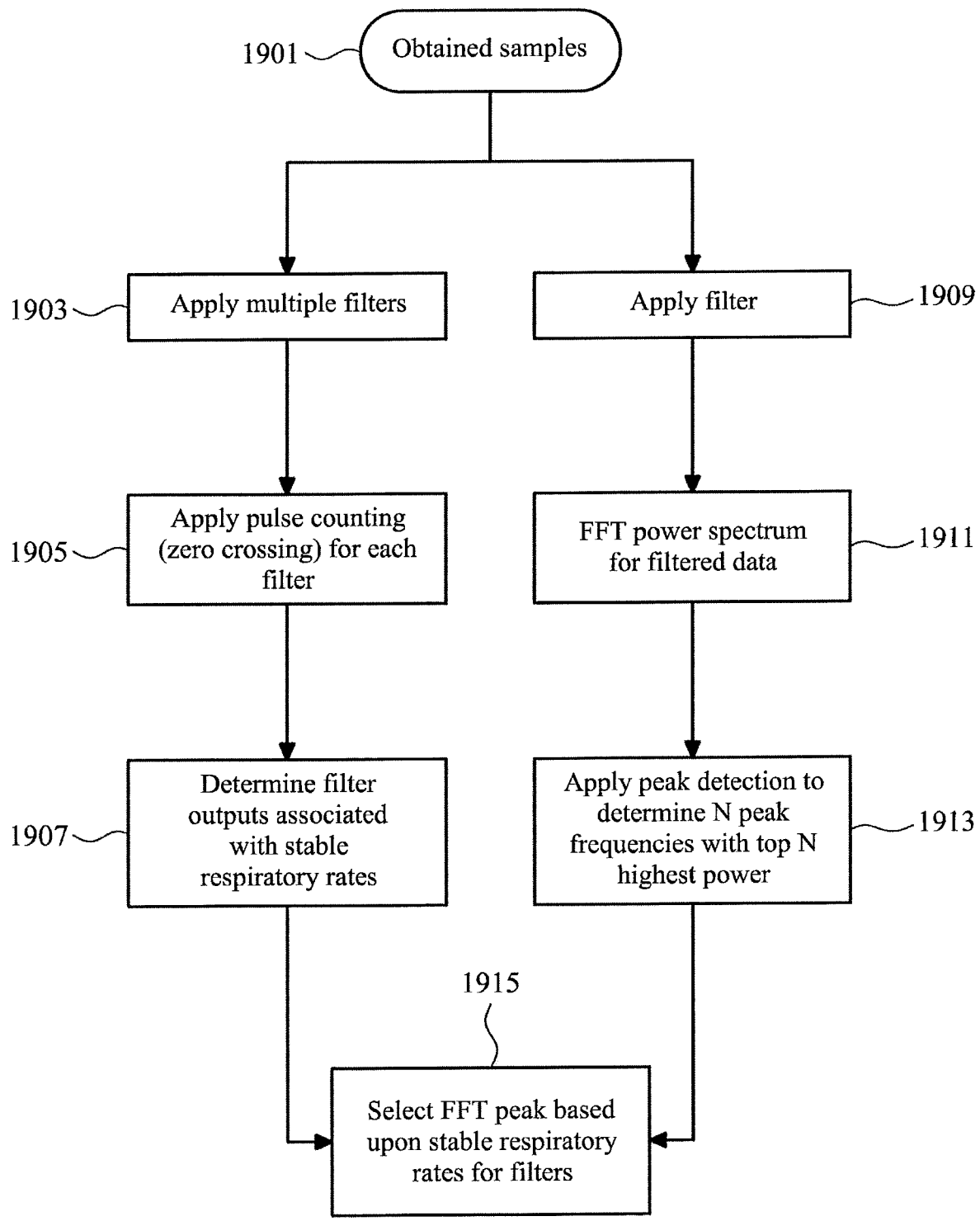
FIG. 18 is an example of an algorithm used in determining respiration rate from the sensor output.

FIG. 18 shows an example of how the relevant peak from the power spectrum of the filtered output corresponding to the patient's respiratory rate can be determined using both zero crossing and FFT techniques.

At step 1901 the sampled data has been obtained. An optional down-sampling step may be applied, if required, so that the sampled data can be processed faster. The method then splits into two branches, one relating to finding the stable respiration rates using the zero crossing technique, or similar, and the other using FFT techniques.

Following the left hand branch, at step 1903 multiple different filters are applied to the sensor output and zero crossing is applied to the output of each filter at step 1905 to perform pulse counting and determine the respiratory rate. Stable respiratory rates for each filter may be established, at step 1907, as described above and shown in FIG. 17.

Following the right hand branch, at step 1909 a filter is applied to the sensor output and then at step 1911 the FFT power spectrum is obtained for the filtered data. As described above, the filter applied prior to obtaining the FFT power spectrum may be the broadest bandwidth filter applied in the multiple filter step 1903, although other filter ranges, including broader filter ranges, are possible. Peak detection is then applied at step 1913 to the FFT to obtain a predetermined number of peaks having the highest power, for example the highest four peaks from the FFT. The peaks may then be ordered according to their power value, for example they may be ranked from lowest power to highest power.

Once the various peaks in the FFT have been determined, the next stage, at step 1915, is to determine which of the peaks is the best candidate for corresponding to the respiratory rate of the patient. This is done by comparing the stable respiration rates determined using multiple filters with cycle counting to identify the best candidate peak. For example, the comparison may be based upon the statistical properties of the stable respiration rates, including the average and spread.

Figure 19A:
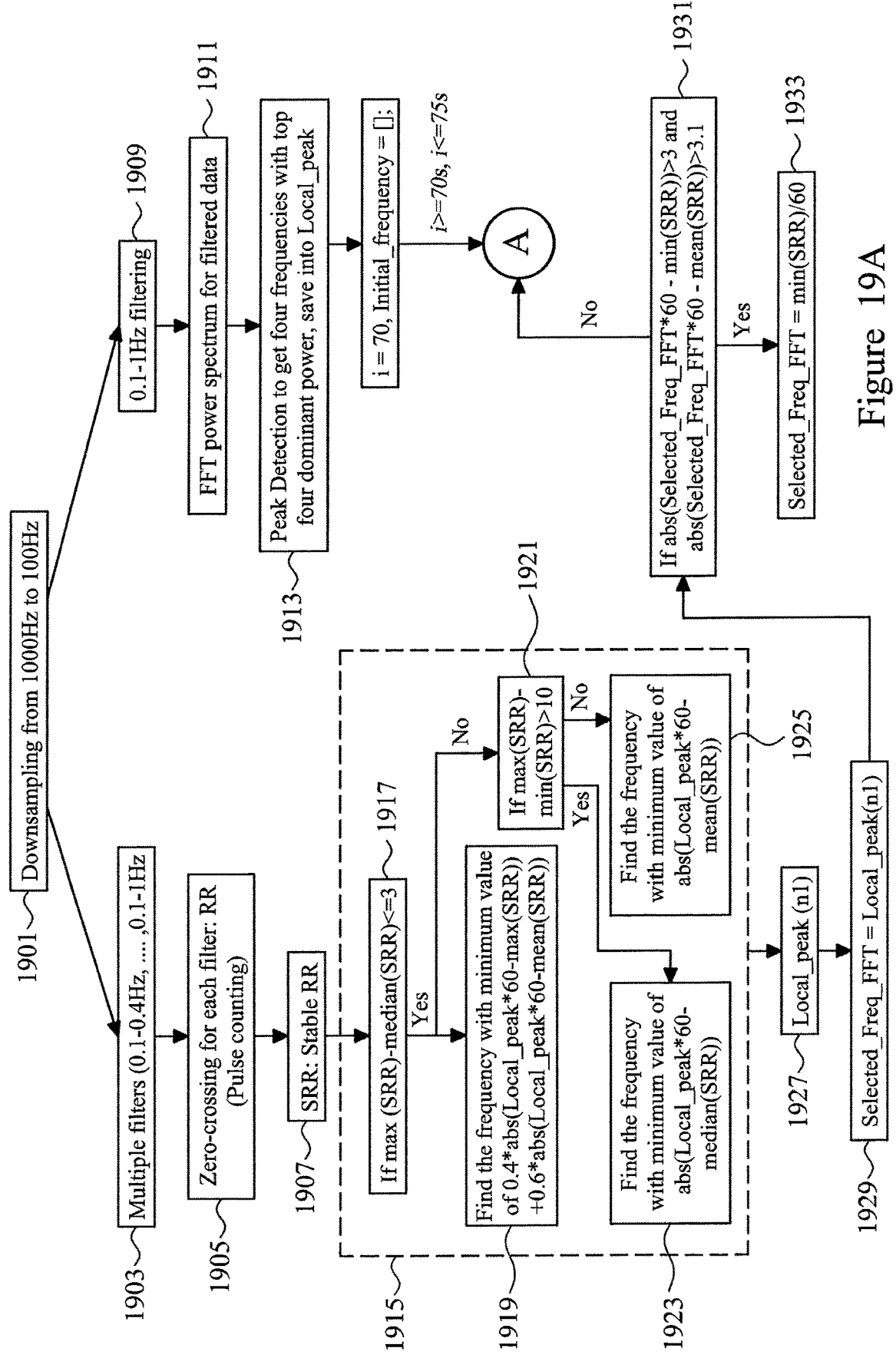
FIGS. 19A and 19B are a more detailed example of an algorithm according to FIG. 18.
Figure 19B:
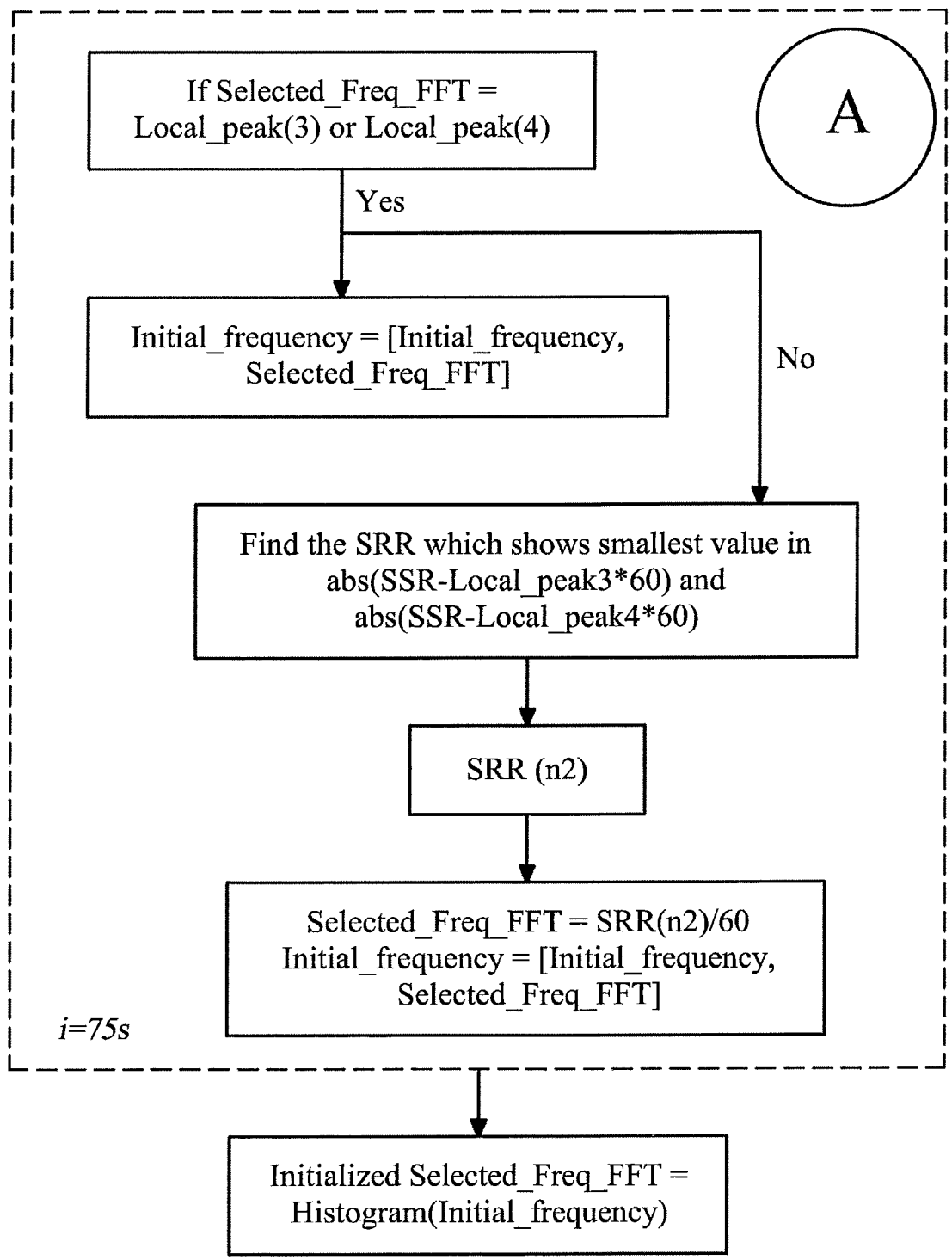

FIGS. 19A and 19B show a more specific example of the method of FIG. 18. The method of FIGS. 19A and 19B can be used as an initialization stage for selecting the initial value for the selected frequency from the FFT.

Steps 1901 to 1913 are the same as those described in relation to FIG. 18 and will not be described again here.

Box 1915 in FIG. 19A shows a more detailed example of step 1915 from FIG. 18, wherein a number of criteria are applied to select the optimum candidate frequency peak from the FFT power spectrum based upon the spread of stable respiratory rates determined according to steps 1903 and 1905.

In this example, at step 1917 the difference between the maximum stable respiratory rate is compared with the mean or median stable respiratory rate as determined across all the filters using zero crossing or similar repeating pattern, or cycle counting techniques. If the result is within a first predetermined range of breaths per minute or equivalent, i.e. less than or equal to a first predetermined value, then the peak that is selected from the FFT is the peak having a minimum value for a particular function. This may be a function of the respiratory rate associated with the peak frequency (i.e. peak frequency multiplied by 60 to determine breaths per minute), the maximum stable respiratory rate and the mean or median stable respiratory rate. In particular, the peak may be selected as the peak having a minimum value for a weighted combination of the difference between the peak BPM value and the maximum stable respiratory rate, and the difference between the peak BPM value and the mean or median stable respiratory rate. An example is given at step 1919. If the result is not within the predetermined range, i.e. it is greater than the predetermined value, then the peak that is selected may be determined based upon one or more further functions of the respiratory rate dependent upon the peak frequency and the median or mean stable respiratory rate. For example, if it is determined at step 1921 that the difference between the maximum stable respiratory rate and the minimum stable respiratory rate is outside a second predetermined range of breaths per minute or equivalent (i.e. greater than a second predetermined value), different to the first predetermined range (or value), then one function, 1923, may be applied, and if the difference is within the second range then a different function, 1925, may be applied. The first function may determine the peak with the minimum value for the difference between the peak BPM value and the median stable respiratory rate. The second, different, function may be to determine the peak with the minimum value for the difference between the peak BPM value and the mean stable respiratory rate. The method therefore, at step 1927, identifies a peak, local_peak (n1), within the FFT power spectrum that corresponds to the most likely candidate for the patient's respiratory rate. The identified peak can then be used to initialize other values as will be described below.

Optionally further functions may be applied, resulting in a different peak being identified from the FFT as the best candidate for respiratory rate. These further functions may be determined based upon experimental results and experience. An example of such a function is shown in FIGS. 19A and 19B, whereby if a certain criteria is met at step 1931, then a different peak is selected at step 1933.

In the particular example of step 1931, the function to select a peak from the FFT depends upon the selected FFT peak according to process 1915 and the minimum and mean SRR values. In this specific example, if the respiratory rate according to the difference between the selected FFT frequency respiratory rate and the minimum SRR value is greater than a first predetermined value, and if the difference between the selected FFT frequency respiratory rate and the mean SRR value is greater than a second predetermined value, then the selected FFT frequency is set equal to the equivalent frequency of the minimum SRR value. Otherwise, another function may be applied.

Another example of such a function, which may be applied as an alternative or in addition to any other additional functions, is shown as "A" in FIG. 19A, and shown in more detail in FIG. 19B. This function determines whether the peak selected by process 1915 is the highest or second highest peak identified in the FFT (peak three or four where the four highest peaks are determined). If so, then the peak selected by process 1915 is retained, and used to determine the initialization frequency. Otherwise a different selected frequency is obtained based upon the respiratory rates determined according to steps 1903 and 1905, particularly by selecting the respiratory rate closest in equivalent value (frequency or rate) to the highest or second highest peak determined according to the FFT.

In the example of FIG. 19B, the matrix "initial_frequency" saves the Selected_Freq_FFT at each step as a new element of the matrix. The matrix initial_frequency=[initial_frequency, Selected_Freq_FFT] indicates that the initial_frequency keeps increasing the dimension of the matrix when the result of Selected_Freq_FFT is saved at each step, or sampling window, as a new element for the initial_frequency matrix. A storage means such as a table or other appropriate means could be used instead of a matrix.

The Histogram function of FIG. 19B refers to applying a statistical method to the initial_frequency matrix. For example, this histogram function may include the counting of frequency of each value that appears in the matrix initial_frequency, and selecting the value that appears most frequently as the value for "Initialized Selected_Freq_FFT".

The initialized value for the selected FFT peak "Selected_Freq_FFT" can be used to initialize one or more further parameters. For example:

i) Select_Pulse_From_StableRR—the stable respiratory rate pulse used in the weighted average may be identified based upon the selected frequency determined from the processing of the FFT data. For example, the "Selected_Freq_FFT" value determined as described in relation to FIGS. 18, 19A and 19B. The Select_Pulse_From_StableRR may be determined by comparing Selected_Freq_FFT to the various stable respiratory rates for the different filters, and selecting the stable respiratory rate that is closest to the Selected_Freq_FFT value.

ii) Array_Select_Pulse_From_StableRR—a circular buffer that stores the latest 15 s of results for Select_Pulse_From_StableRR.

And also historic information, for example:

iii) Avg5Sec_Select_Pulse_From_StableRR: average of Select_Pulse_From_StableRR data for the last 5 s results.

iv) Avg15Sec_Select_Pulse_From_StableRR: average of Select_Pulse_From_StableRR data for the last 15 s results.

Figure 20:
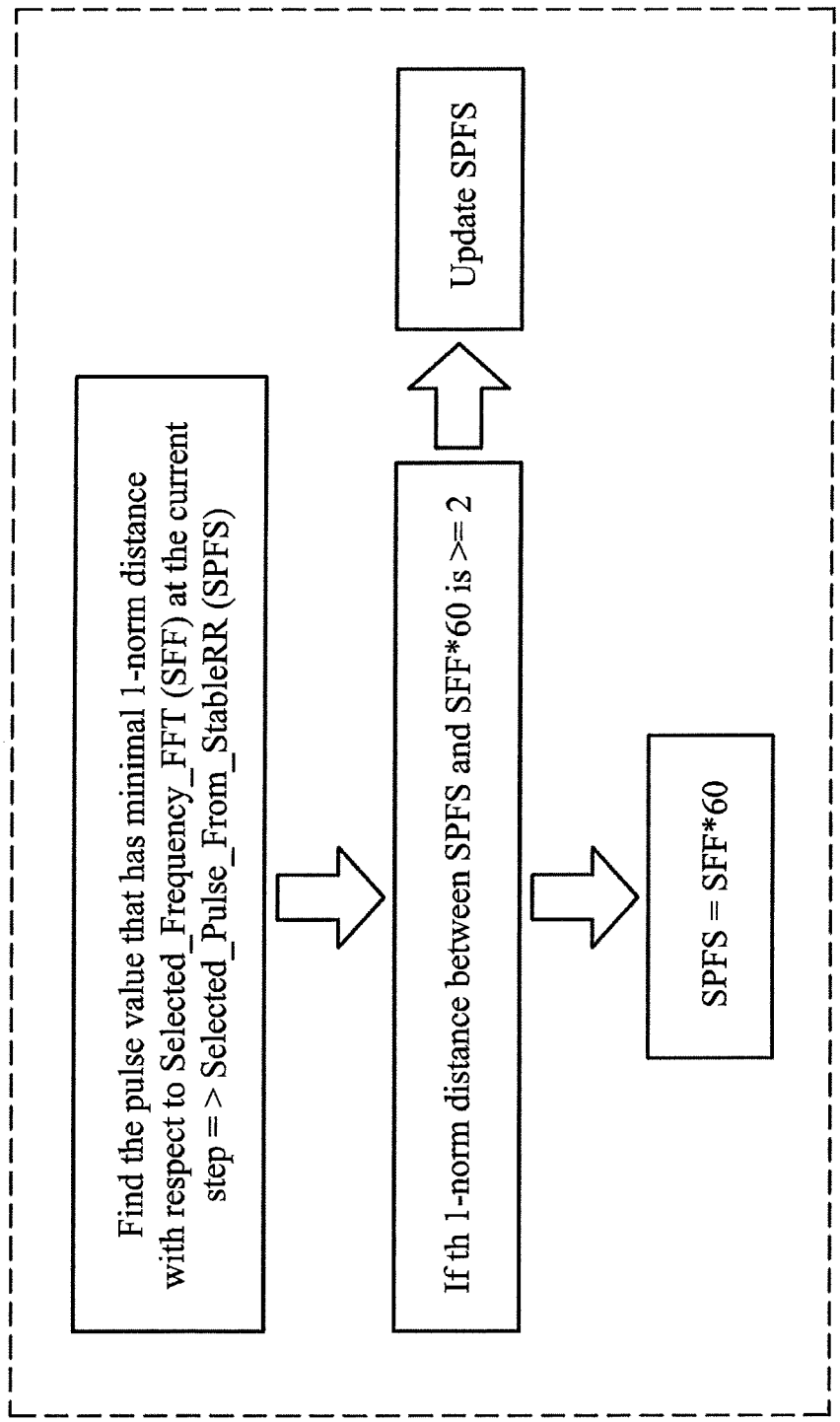
FIG. 20 is an example of logic that may be applied to determine a selected stable respiratory rate from the stable rates determined in accordance with FIG. 18 or FIGS. 19A and 19B.

FIG. 20 provides an example of the logic for determining the parameter Select_Pulse_From_StableRR. Avg5Sec_Select_Pulse_From_StableRR and Avg15Sec_Select_Pulse_From_StableRR can be calculated accordingly as historic information for Select_Pulse_From_StableRR.

After initialization the FFT is monitored to determine whether the frequency spectrum changes, and therefore whether a new frequency needs to be selected, to update the respiratory rate. The selected frequency from the FFT (Selected_Freq_FFT) is continually determined, along with the respiratory rates determined using the multiple filters. The results are combined according to the weighted average to update the respiratory rate. As mentioned previously, the procedure may be applied using a moving window of samples. The window may be, for example, 70 seconds in duration. Initialization occurs after the first window of samples has been collected, so for example windows of data from the $70^{th}$-$75^{th}$ seconds may be used for initialization. Afterwards (e.g. from the $76^{th}$ second), the logic of updating the output respiratory rate is still based upon the two streams of information (SRR by multiple filters and Local_peak from FFT), in a continuous and iterative process.

In order to determine a candidate peak for updating the selected frequency the FFT peaks may be sorted according to height in a similar manner to the initialization stage. The peaks may be further filtered according to desired selection criteria such as how close their equivalent values are (when converted to a respiratory rate) to the selected stable respiration (Select_Pulse_From_StableRR) and/or how close they are to the previously selected FFT frequency (Selected_Freq_FFT). The accumulated historical data above, or similar, may be used for these comparisons.

Candidate peaks are stored in a buffer, e.g. as values for an intermediate metric "Tracking_Val." A determination may be made as to the number of times that the filtered peaks occur, and the selection of a new candidate value for Selected_Freq_FFT may require that value to have occurred a minimum number of times over the period being analyzed so as to distinguish the peak over noise.

Once saved in the buffer, a count may be undertaken to determine how many times each candidate local peak occurs, with the selected frequency from the FFT (Selected_Freq_FFT) being the peak that occurred most often.

Figure 21A:
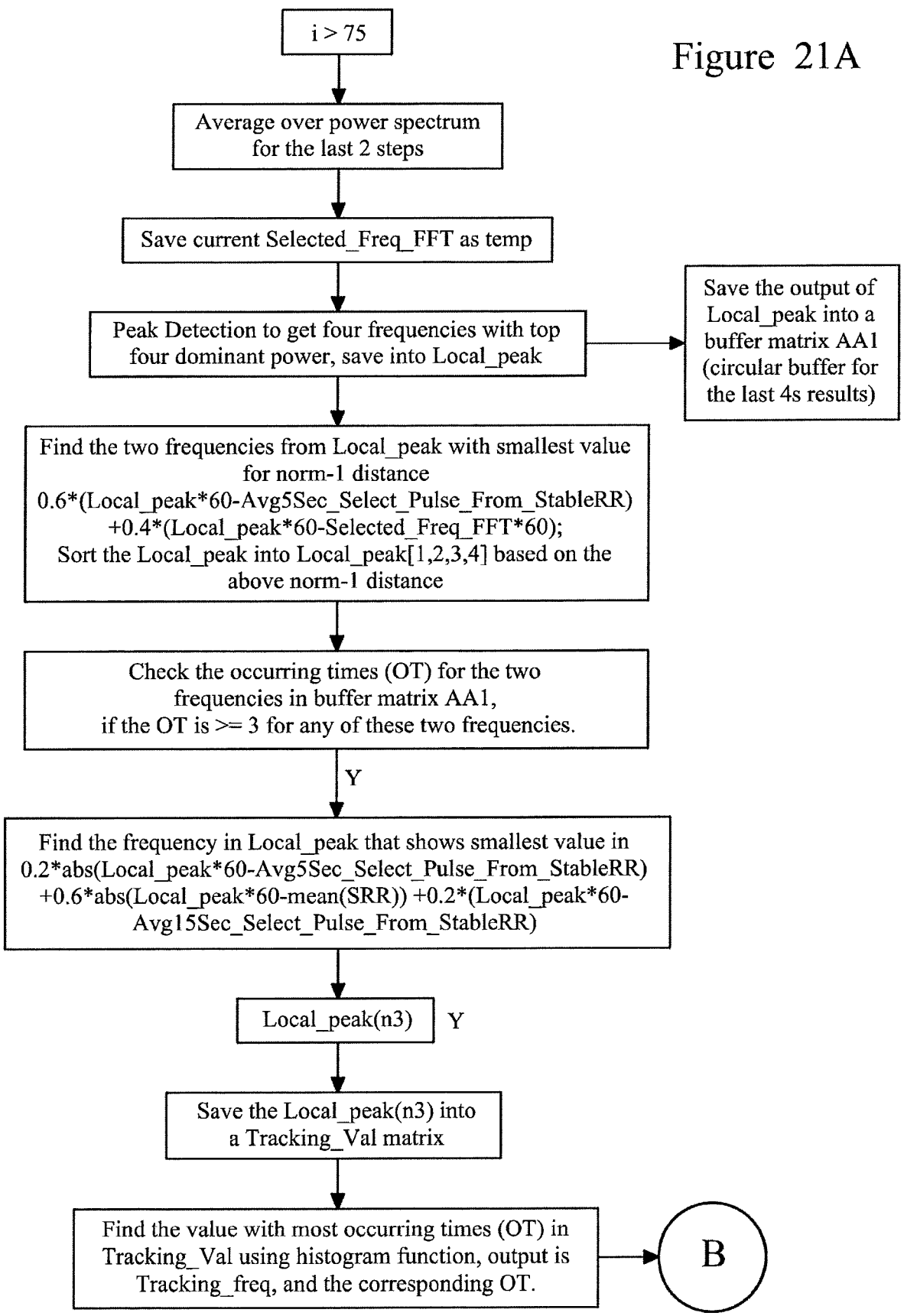
FIGS. 21A and 21B are an example of an algorithm used in updating respiration rate from the sensor output.

FIG. 21A shows an example of a method that may be employed to update the peak selected from the FFT during operation, after initialization.

Figure 21B:
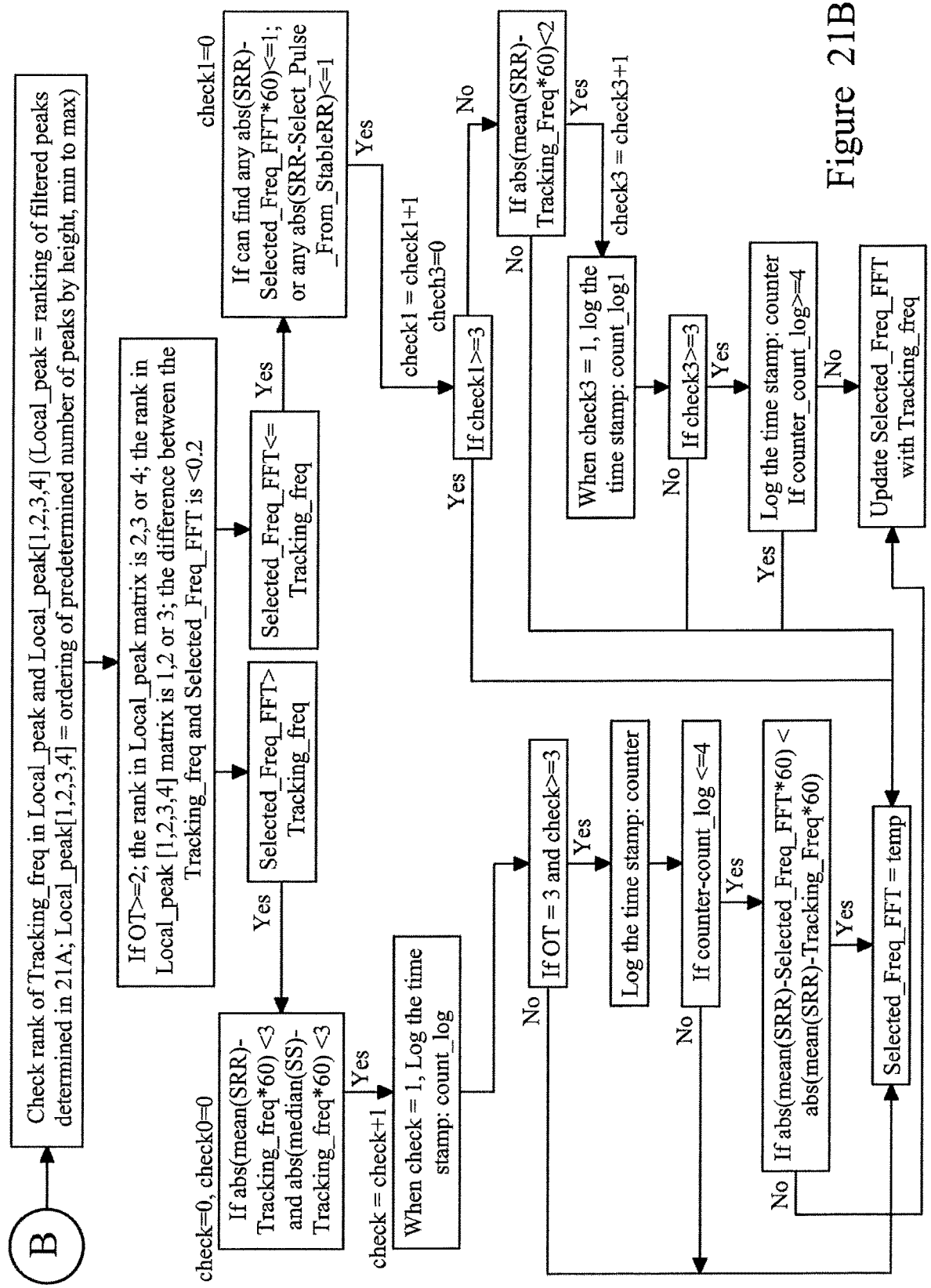

An optional set of additional checks may be applied to determine whether or not to update the Selected_Freq_FFT value, or to retain the previously selected value. These further checks may be determined based upon experimental results and experience. These optional checks are represented by "B" in FIG. 21A, and an example of such a set of check functions is shown in FIG. 21B. One or more of these example checks may be performed in any order as appropriate.

Optionally, a separate check may be performed to determine whether or not to update the value for Selected_Freq_FFT when a large change in respiratory rate would result. A large change in respiratory rate may be from 12 BPM to 18 BPM for example. This check function speeds up the process of determining whether or not to update the value for Selected_Freq_FFT.

Figure 22:
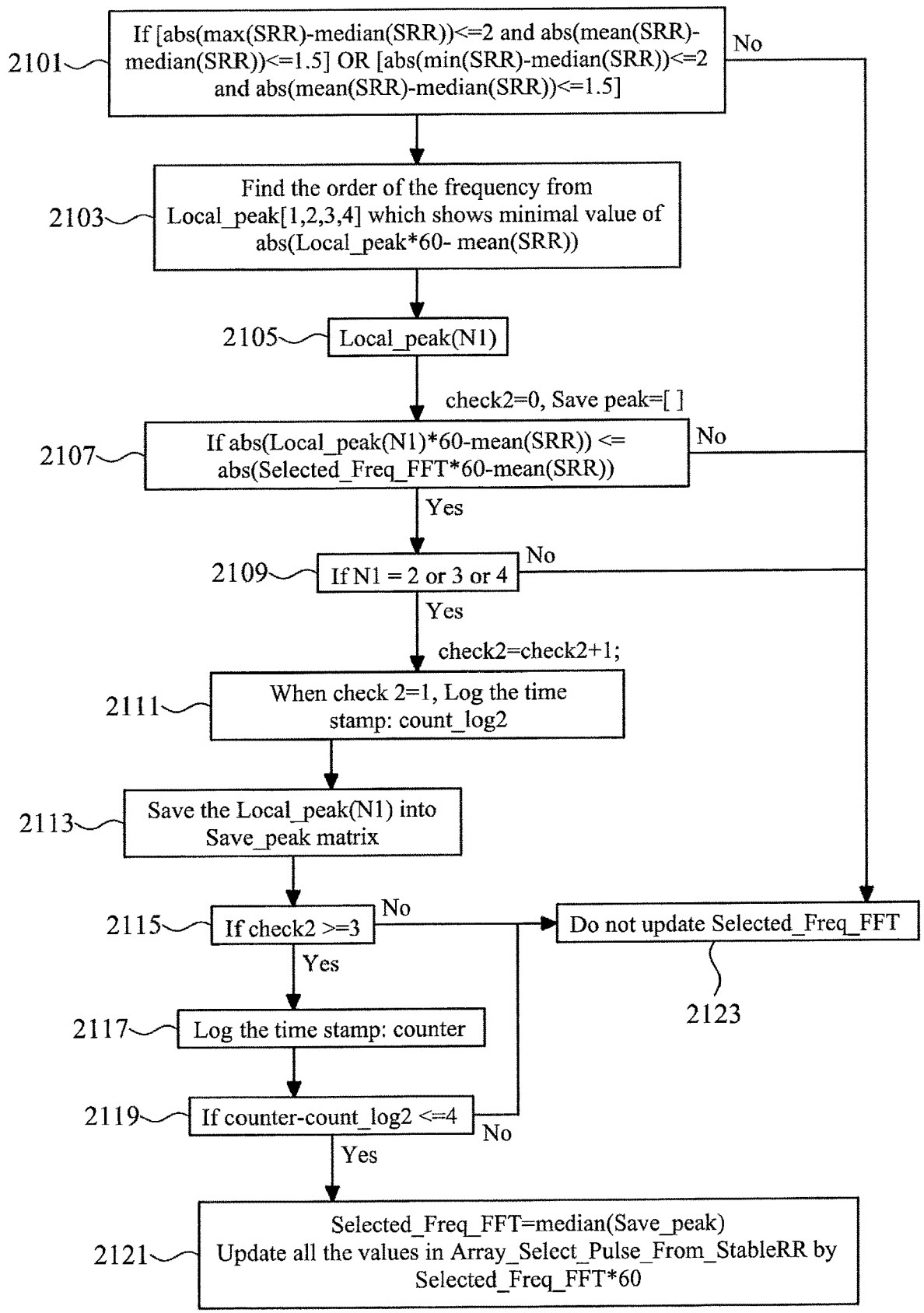
FIG. 22 is an example of an algorithm used in updating respiration rate from the sensor output.

FIG. 22 shows an example of a set of optional checks for this purpose. An initial criteria to be met in order for a change to occur is whether the spread of values determined as stable respiration rates (Stable RR) using the multiple filters falls within predetermined values. For example, at step 2101 it is determined whether the variation of the maximum or minimum SRR from the mean, and the mean from the median, are less than respective predetermined values. If the variation is greater than that provided for by the predetermined values then no update to the Selected_Freq_FFT value is made.

Subsequently, the value for the local FFT peak whose equivalent respiratory rate (i.e. scaled to respiratory rate) is closest to the mean SRR value is determined and this local peak is identified. If the equivalent respiratory rate for this identified local peak is further from the mean SRR value than that of the current Selected_Freq_FFT then the value for Selected_Freq_FFT is not updated. An example of this is shown at steps 2103 to 2107.

A check is performed to determine whether the identified local peak is one of the highest peaks within the FFT or not. For example, if the identified local peak is the highest or the second highest, or in another example one of the first, second or third highest, peak within the FFT then it will be further considered as an update to the currently used Selected_Freq_FFT. Otherwise the value for Selected_Freq_FFT is not updated. An example of this is shown at step 2109.

Further checks may be performed as indicated in FIG. 22. For example, the check "check2" is a count of the frequency for N1=2 or 3 or 4 (i.e. how many times it occurs). In particular, check2 may be a determination of the number of times that a particular peak of a particular frequency is determined to be the highest peak n1.

Although described in a particular order, one or more of the checks of FIG. 22 may be performed in any order, as appropriate.

Further checks may be performed to determine whether or not the value for Selected_Freq_FFT should be updated. One further check can be performed based around whether or not the current value for Selected_Freq_FFT is equal to the highest peak within the FFT. In most cases the current value for Selected_Freq_FFT will also be the highest peak within the FFT, but for the occasions where this is not the case further checks can be performed to determine if the value for Selected_Freq_FFT should be updated. This may involve checking whether the respiratory rate associated with the highest peak is within a predetermined value of any of the SRR values determined for the multiple filters, and determining whether this occurs more than a certain number of times in a certain number of sample processing steps. If it is a recurring feature then the value for Selected_Freq_FFT can be updated, otherwise it is not updated.

Motion artifacts, caused by movements of the patient, can be problematic in embodiments described herein. Motion artifacts are caused by patient movements such as turning to their left or right, or getting up, and can last for a relatively long time. If data that is contaminated with the artifact covers a very broad window of samples and is then rejected by the algorithm, lots of data may be wasted and the recovery time after the motion artifact is introduced will be significantly prolonged. In addition there may sometimes be a baseline drift of the detected signal after a motion artifact is introduced. This is caused by changes of the patient position, with sensor signal strength altered as the patient settles into a new position after the movement. Without additional processing to re-adjust the baseline of the signal the pulse counting result will be affected, leading to inaccuracy in the RR result.

Figure 23A:
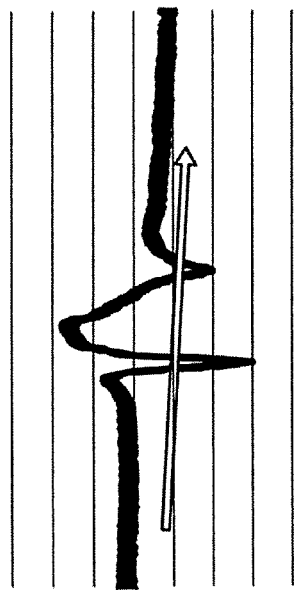
FIGS. 23A and 23B show a representation of a large and small motion artifact in the sampled data respectively.
Figure 23B:
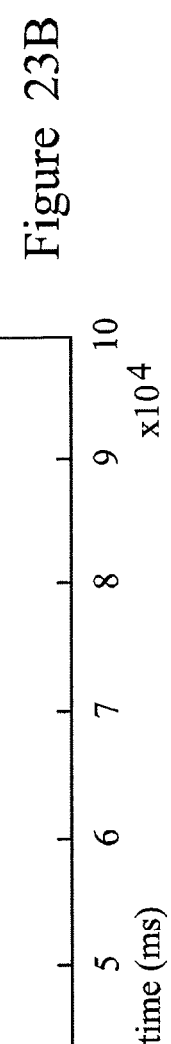

FIG. 23A shows a large motion artifact, in which the signal baseline changes after the motion artifact is introduced. FIG. 23B shows a small motion artifact. A large artifact is one for which the change in detected signal is large compared with the average previously detected signal; a small artifact is one for which the change in detected signal is small compared to the average previously detected signal.

As alluded to above, one option is simply to discard data samples containing artifacts, however such a system is inefficient because the respiratory rate determination calculation would need to be restarted after the discarded data, which introduces delays caused for example by the need to discard data near to the edge of a sampling window. This can introduce delays of 30 seconds, for example, into the determination of an updated respiratory rate. It has been appreciated that samples containing artifacts do not need to be entirely discarded.

Figure 24:
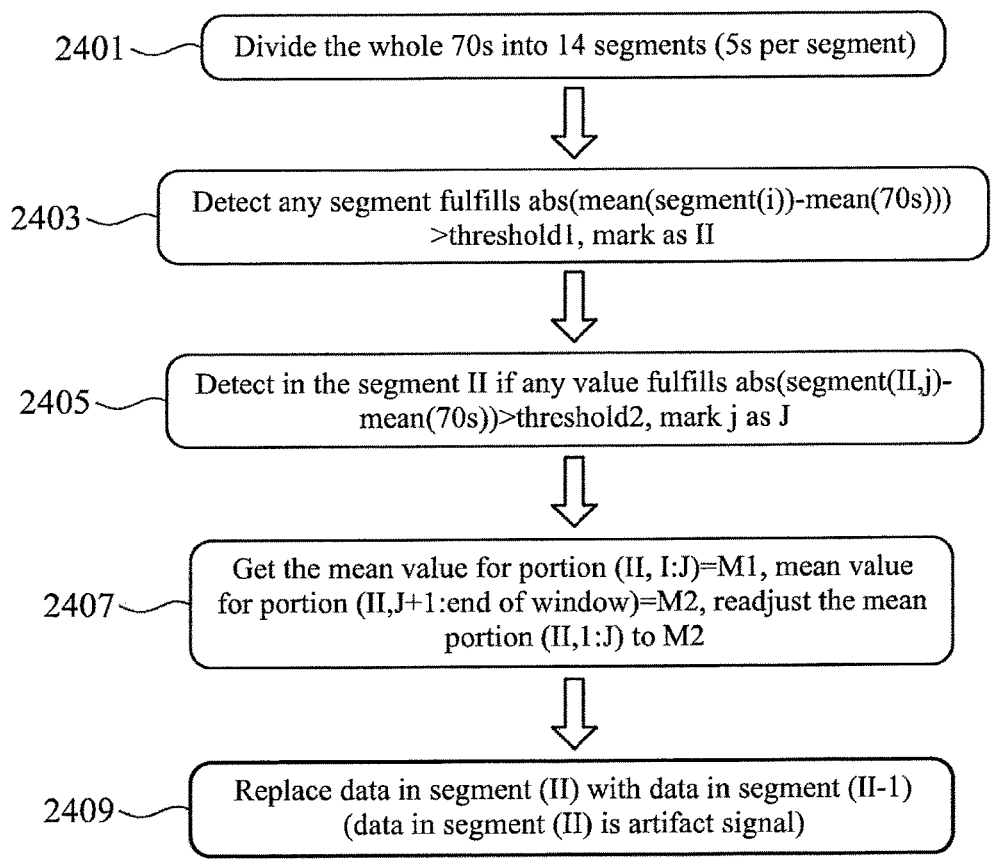
FIG. 24 shows an example of a motion artifact detection and removal method.
Figure 25:
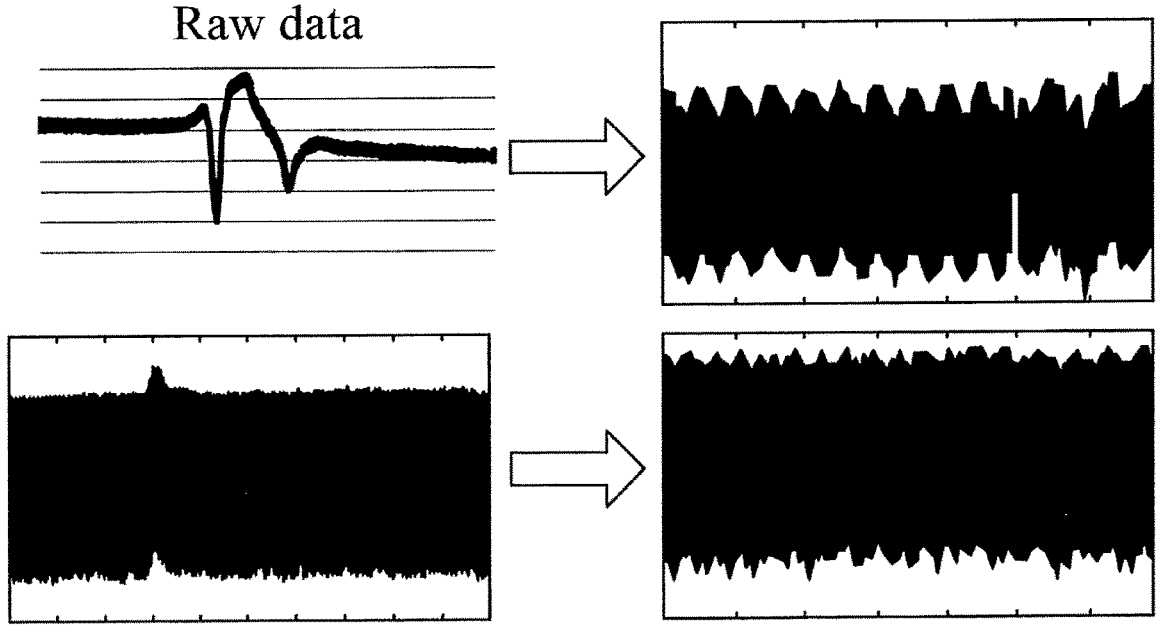
FIG. 25 shows examples of sample data for which motion artifacts have been removed.

A generalized motion artifact detection and removal method may be applied by an algorithm, and will be described in relation to FIG. 24, which provides a specific example of such an algorithm. The method provides a way of linking data obtained before and after the motion artifact to avoid the need to re-start the SRR calculations as a result of motion artifacts.

It should be noted that whilst this method is being applied to the methods described herein for determining stable respiration rates, it can be applied to any such method, or more broadly applied to correcting for motion artifacts in bio-signals, where moving windows are used. This may include EEG signals, heart rate signals etc.

According to the method a moving window is used and the window of samples is divided into segments. Each segment is analyzed to determine if the signal level within the segment meets a predetermined criteria indicative of a motion artifact being present. If the predetermined criteria is met then the relevant segment is deemed to contain a motion artifact signal, and the segment is replaced with another segment that did not meet the criteria, for example the immediately preceding segment that did not meet the criteria.

The predetermined criteria may be a variation of a statistical parameter of the segment from the corresponding statistical parameter for the entire window. In particular the criteria may be whether the average (e.g. mean) value of the signal for the segment differs from the average (e.g. mean) value of the signal for the entire window by a predetermined amount.

Optionally, the mean of the signal may be adjusted over certain portions to account for a change in the baseline after the motion artifact is introduced.

In a particular example of the method a window of samples is divided 2401 into X segments, each of Y seconds in duration. In one example the window length may be 70 seconds long, and is moved on by a step of 1 second each time. The length of the segments is selected to give sufficient resolution to resolve motion artifacts. According to experiment, motion artifacts typically last between 7 and 20 seconds. The segment length is selected to be less than the shortest anticipated motion artifact, and in this example is 5 seconds.

A determination 2403 is then made, for each segment, as to whether the mean signal value for the segment varies by a certain amount from the mean signal value for the whole window. In particular, it may be determined whether the absolute value of the difference between the mean for the segment and the mean of the window exceeds a particular threshold T1. Any segment fulfilling this criteria is identified, for example they may be marked as "II," and may be replaced 2409 by data from another segment, such as the immediately preceding segment.

Optionally, for any segment marked as "II," a determination 2405 may be made as to whether any signal value or sample within that segment varies from the mean signal value of the entire window by more than a certain amount, or threshold "T2," different from the threshold T1. If a sample value is detected that exceeds the threshold T2 it is marked (e.g. as "J") or otherwise identified and used to determine portions of the sample window. In particular, a first portion may, for example, extend from the start of the sample window, to the occurrence of the sample J, and a second portion may, for example, extend from the sample after J to the end of the window. Where multiple samples satisfy the criteria to be marked as J, the first portion may extend up to the first sample J in the window and the second portion may extend from, or immediately after, the final occurrence of sample J in the window.

The method may optionally further include determining 2407 the average (e.g. mean) value for the first (M1) and/or second (M2) portions of the window, and adjusting the average value of one of the portions to the average value of the other portion. For example, this adjustment may involve adjusting the mean value of a portion extending from samples 1 to J to the mean value of the second portion (M2).

This further feature of the present disclosure may be combined with any of the embodiments described herein. Steps 2407 and 2409 may be performed in a different order to that shown in the figure. In particular, step 2409 may be performed prior to step 2407 and 2405.

The inventors have also appreciated that there is a potential problem that can occur when determining SRR rates using a combination of multiple filters and FFT derived rates. The problem is the potential for unstable determined SRR rates. In particular, the SRR (stable pulse count) output could occasionally experience a large jump in value as determined using different filter outputs, which may lead to inaccuracy for the respiratory rate. In addition, the output for SRR for each step, or time window, may occasionally experience a big jump across time, i.e. from one sampling window, or step, to another the SRR may have a big deviation from the last step result. Such a variable result in SRR may lead to inaccuracy in the final respiratory result as frequency information is also cross-referenced to the pulse counting result.

Figure 26:
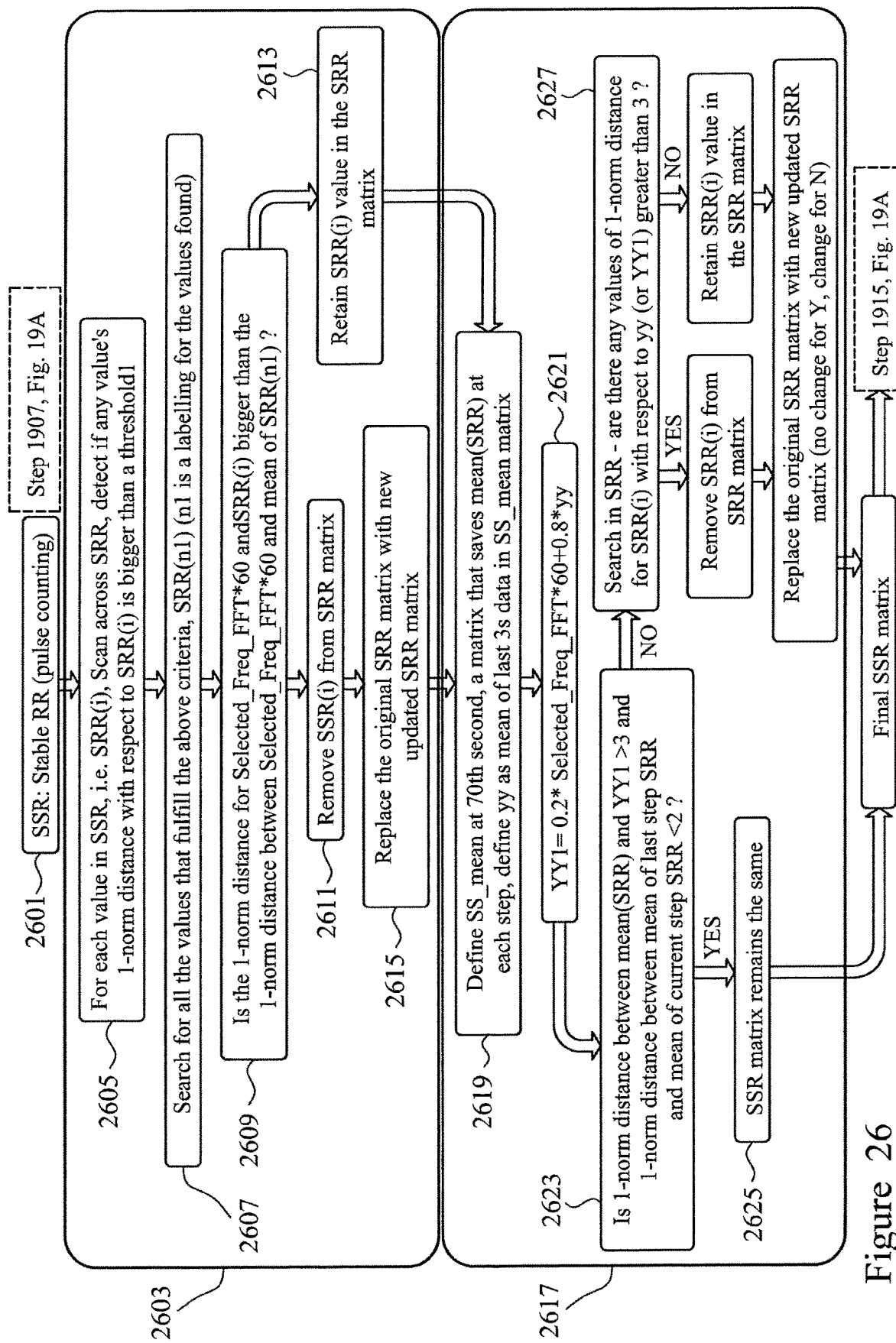
FIG. 26 shows an example of a method for improving the stability of the SRR values obtained according to the methods described herein.

FIG. 26 shows an example of an algorithm for improving the stability of the SRR values obtained. Although generally applicable when determining SRR values using both multiple filters and FFT derived respiratory rates, the method may be employed between steps 1907 and 1915 of FIG. 19A, or in any other method in which SRR values are obtained from multiple filters as described herein.

Generally, FIG. 26 shows two boxes, 2603 and 2617. Box 2603 shows a method for reducing the instability caused by large jumps in SRR values determined between different filters. Box 2617 shows a method for reducing instability caused by variations in SRR between steps. These methods may be applied together or separately, and in any order. These methods may be applied using a sampling window, covering a duration of data of e.g. 70 seconds, which is repeated in steps, for example every second.

Referring to the method of box 2603, the method identifies values for SRR, determined by multiple filters, that deviate too much from other values. By step 2601 SRR values have been obtained based upon multiple filters. The values obtained for each filter can be obtained in the manners described herein. The values obtained for SRR from each filter can then be analyzed 2603 to determine whether the results should be included in subsequent calculations of final SRRs. In particular, this determination can be made based upon a comparison 2605 of each of the various values obtained for SRR by filters with the other values obtained for SRR by filters. If the comparison reveals that the particular SRR is an anomaly then it may be removed.

At step 2605, for each value of SRR, SRR(i), the difference between SRR(i) and the other SRR values are determined. The values may be the absolute difference between the particular SRR value, SRR(i), and the other SRR values. To identify the difference values that may indicate that SRR(i) is anomalous, the difference values may be compared to a threshold "threshold1." If the value is larger than the threshold then the SRR(i) value is considered a possible anomaly. Where the SRR values are stored in a matrix the difference value may be determined as the 1-norm distance, or maximum column-sum, with respect to the SRR(i) value.

Each of the SRR(i) values that have one or more comparison values that exceed the threshold is identified and may be labelled accordingly. For example, as shown in step 2607, each value is labelled as SRR(n1).

The next step is to identify which of the identified SRR(i) values are actually anomalous. This can be performed by comparing each potentially anomalous SRR(i) value with the SRR value determined using the FFT method described herein. At step 2609, the difference between each identified value SRR(i) and a corresponding respiratory rate determined by FFT is determined. The respiratory rate determined by FFT may be the rate determined according to the previous sample window. If the difference is too great then the particular SRR(i) value is removed from further consideration. This may be determined by comparing (i) the difference between the SRR(i) value and the respiratory rate corresponding to the FFT derived value Selected_Freq_FFT*60 with (ii) the difference between the FFT derived value Selected_Freq_FFT*60 and the mean of the SRR(i) values making up SRR(n1). Where the absolute difference (i) is greater than the absolute difference (ii), the particular SRR(i) value is removed from further calculations. Where the absolute difference (i) is less than the absolute difference (ii), the particular SRR(i) value is retained.

Where the SRR values are held in a matrix, the comparison performed may be whether the 1-norm distance between the value for SRR determined using FFT methods and the particular SRR value is greater than the 1-norm distance between the value for SRR determined using FFT methods and the average or mean value of the SRR values deemed to exceed the "threshold1".

Process 2617 determines the difference between the average SRR for a current window and the average SRR for one or more previous sample windows, and removes values of SRR, SRR(i), that may be causing significant variations in these means.

According to the method of box 2617, the mean values for SRR, as determined by the multiple filters, are stored for each step. As shown at step 2619, this may be done using a matrix "SS_mean" for example. Calculation of the mean SRR values may commence after the first window of samples has been obtained. For example, where the moving sample window is 70 seconds in duration the mean SRR values commence being calculated after 70 seconds.

A parameter is defined that is indicative of the immediately preceding historical average values for SRR. The parameter, "yy", may be the average (e.g. mean) of the SRR values determined over a predetermined length of time, such as the preceding few seconds. For example, "yy" may be the mean of the last three seconds of mean SRR data, i.e. the last three seconds of data in the matrix "SS_mean."

A parameter "YY1" is then calculated, at step 2621. The parameter YY1 may simply be the value "yy," in which case no specific calculation is required. Optionally, however, the YY1 value may be a combination of the yy value and the SRR determined using FFT methods ("Selected_Freq_FFT*60). The YY1 value may be a sum of the FFT determined value and the yy value, with particular weightings applied. Preferably the weightings favor the yy value because this value is more closely related to the SRR values determined using multiple filters.

At step 2623 it is determined whether the difference between the mean SRR value for the current window and the value YY1 is outside a particular threshold, having a predetermined value. It is also determined whether the difference between the mean SRR values for the previous step and the current step are outside a particular different threshold, having a predetermined value. The 1-norm distance between the mean SRR value and YY1, and between the mean SRR value of the preceding step and the current step may be used as an absolute difference. The threshold values shown in FIG. 26 are example values for illustration only. The values may be varied based upon experiment, and depending upon the particular arrangement to which the method is being applied.

If the criteria of step 2623 are satisfied then the collection of values of SRR determined by multiple filters, and used for further calculations of SRR, remains unaltered. For example, where these SRR values are stored in a matrix, the SRR matrix remains the same; see step 2625.

If the criteria of step 2623 are not satisfied then a search is performed, at step 2627, to determine whether there are any values for SRR within the store of SRR values that vary by too great an amount from the mean of the last predetermined period of data, yy, or alternatively the value YY1 (either may be applied). If the difference for a given SRR value SRR(i) exceeds a predetermined value then that value SRR(i) is removed from further calculations. In particular, the value may be removed from the SRR matrix. In the example of FIG. 26 the comparison is for values of SRR(i) within the matrix having a 1-norm distance with respect to yy of more than a predetermined value, which may be the same predetermined value as for the 1-norm distance between mean(SRR) and YY1 as used in relation to step 2623. Again, an example of this value is given for reference only. If the predetermined value for any SRR(i) is exceeded then these SRR(i)s are removed from the SRR matrix. If this is not the case then the values are retained or saved in the SRR matrix.

The resulting set of SRR values, from the various different filters, are then used as described herein to determine a final respiratory rate for output by the system, for display or for monitoring.

The air support system, which may be used in embodiments of the present disclosure, may comprise a mattress having at least one inflatable bladder and a control unit. The control unit, which may house the electronics for performing the methods described herein or may be a separate unit, may comprise a main housing and a source of pneumatic pressure carried by the main housing and operable to inflate the at least one inflatable bladder. The control unit may be configured to control inflation of the at least one air bladder.

Figure 27:
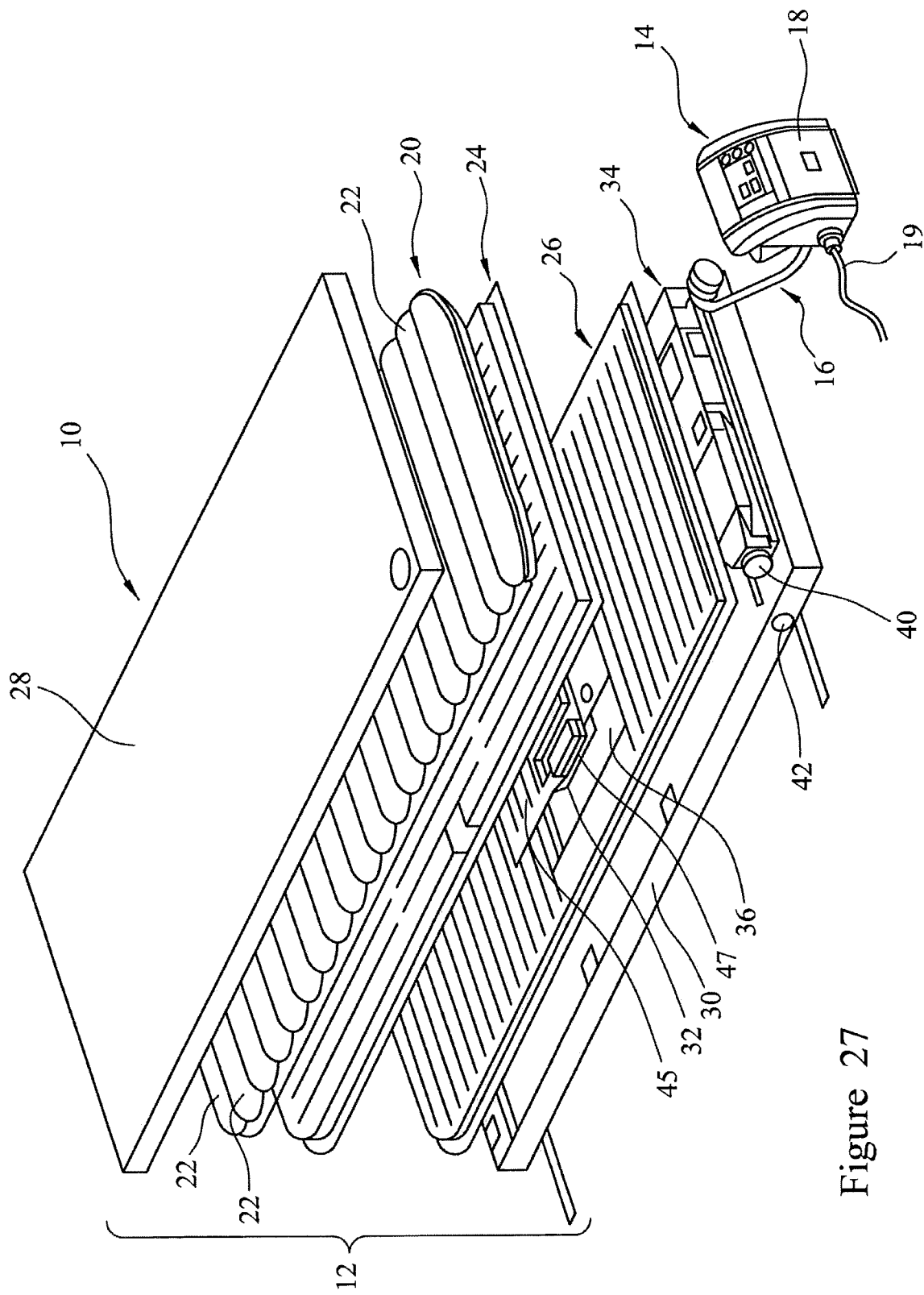
FIG. 27 is an example of a mattress and support unit that may be used in embodiments of the present disclosure.

For illustrative purposes only, an example of the type of mattress to which embodiments of the present disclosure may be applied is shown in FIG. 27. The mattress may, for example, be a mattress of the sort described in U.S. Pat. No. 7,849,545 which is hereby incorporated herein by reference. The mattress system 10 includes a mattress 12 and a control unit 14 that is spaced-apart from the mattress 12 and that is coupled pneumatically and electrically with the mattress 12 by a connector assembly 16 as shown in FIG. 1. The control unit 14 may be configured to provide the mattress system 10 with various functionalities depending upon user desire. For example, one mode of operation may be a continuous low pressure mode and another mode of operation may be an alternating pressure therapy mode. The illustrative mattress system 10 is available commercially and is marketed as the CLINACTIV™ Therapy Mattress System by Hill-Rom Company, Inc.

Illustratively, the mattress 12 includes an upper inflatable bladder layer 20 having a plurality of laterally-extending cells or bladders 22 which cooperate to define various zones of layer 20. For example, a head section zone includes the first three cells 22 of layer 20. These three cells 22 may be fluidly interconnected and are illustratively regulated to the same pressure. The next ten cells 22 form a torso section zone of layer 20. Finally, a heel section zone may include the last seven cells 22 of layer 20 which may be fluidly interconnected with each other and generally regulated to a low target pressure. This target pressure may be independent of the rest of the zones of the layer 20 and can be regulated by electronics within the control unit 14.

The illustrative mattress 12 further includes a pressure sensor 32 and a technical box 34 containing an air distribution system 35 which includes a set of valves 37, associated circuitry 39, and a manifold assembly 33 in fluid communication with the various cells 22 of layer 20 as well as with the first and second air mattress underlays 24, 26. The manifold assembly 33 includes a pneumatic input and a plurality of pneumatic outputs, each of which is associated with its own valve of the set of valves 37. In one embodiment, a first valve is in fluid communication with the group of five bladders 22 of the torso section zone while a second valve is in fluid communication with the second group of five bladders 22 of the torso section zone. The first and second sets of bladders 22 in the torso section zone are arranged alternately and the first and second valves 37 are controlled to inflate and deflate the first and second groups of bladders 22 of the torso section zone alternately when mattress system 10 is operating in the alternating pressure mode, for example, as dictated by the programming of control unit 14 as mentioned above.

Illustratively, the pressure sensor 32 may be positioned within a cut-out section 36 formed in the second air mattress underlay 26 as shown in FIG. 1 while the technical box 34 may be positioned at a foot end of the mattress 12 such that foot ends of the air mattress underlays 24, 26 generally abut the technical box but do not extend over the top of the technical box 34. However, the layer 20 (and particularly the heel zone bladders 22 of the 15 layer 20) may extend over the technical box 34. When the mattress 12 is assembled, the pressure sensor 32 of the mattress 12 may be positioned generally below the torso section zone of the layer 20 in order to sense the pressure exerted by a patient on the torso section zone and provide an output signal to the control unit 14 indicating the sensed pressure.

For illustrative purposes only, more details on examples of the types of sensor that may be used in embodiments of the present disclosure will now be described. The sensor used in embodiments of the present disclosure may comprise at least one capacitive cell. The at least one capacitive cell may include a flat condenser comprising at least one layer of a compressible insulating dielectric material interposed between two layers of conductive material. The support device capable of supporting the body of a person may comprise at least one layer composed of a plurality of air-filled inflatable cells communicating with inflation elements. The condenser may then be disposed under the layer of air-filled inflatable cells and can be connected to an electronic control and regulation device capable of controlling inflation or deflation elements.

In particular, the capacitive sensor may be a sensor of the sort described in U.S. Pat. No. 8,598,893, the content of which is hereby incorporated by reference herein. The described sensor is mainly used to determine the weight of a person resting on a support device.

The layer of compressible dielectric insulating material may comprise a sheet of a synthetic elastomer with a Shore hardness of 45 to 55 Sh. The layer of compressible dielectric material may have a thickness of between 0.3 to 1 mm.

The capacitive cell may be integrated in an oscillator capable of generating a periodic electric signal, wherein the frequency of said periodic electric signal varies as a function of said load pressure within a range of 15 to 30 kHz, with a variation of at least 45 Hz/kg for a weight of 0 to 80 kg applied to the surface of said flat condenser. The sensor oscillator may be coupled to a converter for converting the frequency of the periodic electric signal output by the oscillator to a voltage signal.

The conductive layers may comprise sheets of fabric comprising, at least partially, metallic threads of a non-oxidizing metal. The conductive sheet may comprise woven material made from threads of nickel and threads of a plastic that is at least one of polyester and polypropylene.

The sensor may be used to regulate the inflation air pressure inside a mattress comprising air-filled cells, wherein the at least one layer of compressible dielectric insulating material and the two layers of conductive material have the same rectangular shape of between about 600 and 900 mm long and between about 400 and 600 mm wide, and wherein the total thickness of the at least one layer of compressible dielectric insulating material and the two layers of conductive material when superimposed together is less than 10 mm.

The sensor may comprise at least one capacitive cell including a flat condenser comprising at least one layer of a compressible dielectric insulating material interposed between two layers of conductive material, wherein the at least one layer of compressible dielectric insulating material and the two layers of conductive material are applied directly against each other without interposed connecting layers, wherein the at least one layer of compressible dielectric insulating material and the two layers of conductive material are solidly connected to each other by tack welds that are capable of keeping the at least one layer of compressible dielectric insulating material and the two layers of conductive material in a superimposed position relative to each other.

A support device for use in embodiments of the present disclosure may comprise at least one top layer having a plurality of air-filled inflatable cells communicating with inflation elements, and a sensor for detecting and measuring a load pressure applied to at least some of the air-filled inflatable cells of the plurality of air-filled inflatable cells, the sensor comprising at least one capacitive cell including a flat condenser comprising at least one layer of a compressible dielectric insulating material interposed between two layers of conductive material, wherein said layer of compressible dielectric material has a thickness of between 0.3 to 1 mm, said condenser being disposed under said at least one top layer and connected to an electronic control and regulation device designed to control the inflation or deflation elements for filling or emptying, respectively, said plurality of air-filled inflatable cells of said top layer in such a way that the internal inflation pressure of the air inside the cells is equal to an ideal set point pressure predetermined relative to the load pressure of the body of a person resting on said top layer, measured by said sensor. The flat condenser may be situated on top of a support layer that is more rigid than said top layer, said support layer comprising a closed cell foam layer with a density greater than 50 kg/m$^3$. The top layer may comprise a central zone corresponding to the sacral region of the body of a person reclining on said top layer, of which said cells are individualized and narrower than the adjacent cells of a head zone and a foot zone on either side of said central zone. The top layer may be supported by an air-filled bottom layer constituted from a single parallelepiped cell, and the sensor may be disposed under said bottom layer. The pressure of the air inside said bottom layer may be adjusted by said control and regulation device to the same regulation pressure as said top layer, and said bottom layer comprises a safety valve that is automatically closed by said control and regulation device in order to keep said bottom layer sealed when a leak is detected in said top layer. The flat condenser may rest on a rigid support layer with a thickness less than or equal to 10 mm, and said flat condenser extends appreciably across the entire width of the support device and in relation to a central zone of the support device corresponding to the sacral region of a person reclining on said top layer, and over a length of about 400 to 600 mm in the longitudinal axis of said support device.

A support device for use in embodiments of the present disclosure may comprise at least one top layer having a plurality of air-filled inflatable cells communicating with inflation elements, and a sensor for detecting and measuring a load pressure applied to at least some of the air-filled inflatable cells of the plurality of air-filled inflatable cells, the sensor comprising at least one capacitive cell including a flat condenser comprising at least one layer of a compressible dielectric insulating material interposed between two layers of conductive material, said condenser being disposed under said at least one top layer and connected to an electronic control and regulation device designed to control the inflation or deflation elements for filling or emptying, respectively, said plurality of air-filled inflatable cells of said top layer in such a way that the internal inflation pressure of the air inside the cells is equal to an ideal set point pressure predetermined relative to the load pressure of the body of a person resting on said top layer, measured by said sensor, wherein the at least one layer of compressible dielectric insulating material and the two layers of conductive material are applied directly against each other without interposed connecting layers, wherein the at least one layer of compressible dielectric insulating material and the two layers of conductive material are solidly connected to each other by tack welds that are capable of keeping the at least one layer of compressible dielectric insulating material and the two layers of conductive material in a superimposed position relative to each other.

As mentioned above, the capacitive sensor used in embodiments of the present disclosure may be the same sensor used in the system described in U.S. Pat. No. 8,429,774. This system provides a type of support device, offering a patient functional lateral tilting, that is integrated into the mattress and that is safe. It also can be controlled in terms of the incline angle of the mattress on which the patient lies on the one hand, and on the other, capable of being done cyclically according to the durations of the different stages of the cycle of alternated lateral tilting from one side to the other, in a controlled and reliable manner. To this end, this system offers a device for laterally tilting a patient lying on a mattress, capable of being inserted between said mattress and a bed base or bed frame on which said mattress lies, utilizing the inflatable cells described herein and/or utilizing additional inflatable cells. The lateral tilting device may comprise at least two first and second inflatable cells, pneumatically independent and positioned at least partially symmetrically to each other in relation to a median axis of said tilting device, the shape in the inflated state being capable of creating a lateral incline of the mattress when a first cell is inflated more than the second cell and a lateral incline sloping in the opposite direction when said second cell is inflated more then said first cell, said tilting device being inserted between the mattress and a bed base or bed frame on which it rests, with a median axis of said tilting device positioned so as to make it roughly coincide with a longitudinal median axis of said mattress. By "pneumatically independent," it is understood that said cells are capable of being inflated with air or deflated independently and differently from one another and if applied using different inflatable cells to those already used in the support mattress, independently and differently from the inflatable cells comprising said mattress under which the tilting device is inserted.

Whilst embodiments have been described primarily in relation to a capacitive sensor positioned at the underneath of an air-filled mattress, aspects of the present disclosure may be applied to capacitive sensors located in any suitable position on any type of mattress, including on top of the mattress, integrated to a surface, a frame or any other device close to the bed/patient for diagnostic or patient monitoring. In particular, this may apply to the use of a combination of respiratory rates determined for multiple filters with peaks determined using FFT techniques to determine an actual respiration rate.

Embodiments have been described that activate alarms based upon determined respiratory parameters such as respiration rates. It is not necessary to provide alarms, and embodiments that provide the determined respiratory parameters to a display, or to another output, are also useful to the care provider.

The invention claimed is:

1. A system for monitoring a patient on an air support system, the system comprising:
 a capacitive sensor system having a capacitive sensor positioned at the underside of an air filled mattress;
 a respiration signal processing module that receives the output of the capacitive sensor system and is configured to monitor patient respiration by:
 periodically sampling the capacitive sensor system output to obtain measurements of incremental body displacement;
 analyzing a plurality of the samples to determine one or more values for parameters of patient respiratory rate;
 determining when one or more of the parameter values indicate abnormal respiration;
 wherein analyzing the plurality of the samples to determine one or more values for parameters of patient respiratory rate comprises:
 performing a cycle counting technique on the plurality of samples to determine a first value indicative of respiratory rate;
 separately performing analysis of a power spectrum of the plurality of samples to determine a frequency corresponding to a second value indicative of respiratory rate;
 combining results of the cycle counting technique with results of the analysis of the power spectrum by averaging the first and second values to determine an output value indicative of patient respiratory rate;
 analyzing the plurality of samples comprises determining a periodic variation in the output of the capacitive sensor system using a predetermined number of accumulated samples, and determining the patient respiratory rate based upon the periodic variation, the periodic variation in the output of the capacitive sensor system is determined using a moving sample window; and
 determining when one or more of the parameter values indicate abnormal respiration comprises comparing the patient respiratory rate with an upper and/or lower threshold value, wherein the patient respiratory rate passing beyond the upper and/or lower threshold value indicates abnormal respiration.

2. The system of claim 1, further comprising one or more band pass filters each having an upper frequency cut-off of 2 Hz or less, and a lower frequency cut-off of 0 Hz or more.

3. The system of claim 1, wherein performing the cycle counting technique on the plurality of samples to determine the first value indicative of respiratory rate comprises:
- separately applying each of a plurality of band-pass filters to the output of the sensor, or an output derived from the output of the sensor, each band pass filter having a different band-width to the other filters;
- performing a cycle counting technique to determine a value indicative of respiratory rate associated with the output of each of the band-pass filters;
- selecting one or more of the values indicative of respiratory rate determined from the output associated with the filters for combination with the results of the analysis of the power spectrum.

4. The system of claim 3, wherein selecting one or more of the values indicative of respiratory rate determined from the output comprises determining, for each of the outputs associated with a band-pass filter, whether the respiratory rate is stable by comparing the output associated with each band pass filter with the output of one or more other filters and determining whether the determined respiratory rate is within a predetermined range of the respiratory rate determined using the one or more other filters.

5. The system of claim 4, wherein the filters are ordered according to bandwidth and comparing the output associated with each band pass filter with the output of one or more other filters comprises comparing the output for each filter with that of its neighbouring filters.

6. The system of claim 1, wherein performing analysis of the power spectrum of the plurality of samples to determine a frequency corresponding to the second value indicative of respiratory rate further comprises determining N highest peaks within the power spectrum and identifying, from the determined peaks, the peak associated with respiration rate based upon the cycle counting technique.

7. The system of claim 1, wherein combining the results of the cycle counting technique with the results of the analysis of the power spectrum to determine the output value indicative of patient respiratory rate comprises determining a weighted average of the first and second values determined according to the cycle counting technique and the power spectrum analysis technique.

8. The system of claim 3, wherein the respiration signal processing module is further configured to:
- compare the value of each of the values indicative of respiratory rate determined from the output associated with the filters with a predetermined threshold to determine a set of values SRR(n1);
- for each value that exceeds the threshold, compare (i) the difference between that value and the respiratory rate determined based upon the results of the analysis of the power spectrum with (ii) the difference between the results of the analysis of the power spectrum with the average value of the set of values SRR(n1); and
- discard one or more values indicative of respiratory rate determined from the output associated with the filters based upon the comparison.

9. The system of claim 3, wherein the periodic variation in the output of the capacitive sensor system is determined using a moving sample window and the respiration signal processing module is further configured to:
- for each sample window, determine the average value of the values indicative of respiratory rate associated with the output of each of the band-pass filters;
- compare the average value determined for the current window with a value determined based upon the average value of one or more previous windows;
- where the comparison indicates that the average value of the current window varies from the average value of one or more previous windows, determine whether any of the values indicative of respiratory rate associated with the output of one of the band-pass filters varies by more than a predetermined amount from a value determined based upon the average value of the one or more previous windows, and if so, discard those values indicative of respiratory rate.

10. The system of claim 1, wherein the respiration signal processing module is further configured to:
- divide a current sample window into a plurality of segments;
- determine, for each segment, whether the average signal value of the segment differs from the average signal value of the sample window by more than a predetermined amount;
- determine, for each segment for which the average signal value of the segment differs from the average signal value of the sample window by more than a predetermined amount, whether any sample value, J, within the segment differs from the average signal value of the window by more than a predetermined amount;
- divide the window into at least two portions, the first portion spanning from the first sample to a sample J, and the second portion spanning from a sample J to the end of the window;
- adjust the sample values for the first portion such that the average of the first portion conforms to the average of the second portion; and
- replace segments for which the average signal value of the segment differs from the average signal value of the sample window by more than a predetermined amount with segments for which this is not true.

11. The system of claim 1, further comprising a pressure signal processing module that receives the output of the capacitive sensor system and is configured to determine the pressure exerted by the patient's body or the penetration of the patient's body into given areas of the mattress;
wherein:
- the mattress comprises a plurality of inflatable cells communicating with inflation elements; and
- the system further comprises an electronic control and regulation device connected to the pressure signal processing module, the electronic control and regulation device configured to control the inflation elements for filling or emptying, respectively, said plurality of air-filled inflatable cells in such a way that the internal inflation pressure of the air inside the cells is equal to a set point pressure predetermined relative to the load pressure of the body of a person resting on the mattress measured by said sensor;
- wherein the electronic control and regulation device is further configured to receive a signal indicating that abnormal respiration has been detected, and to cause the repositioning of the body of a person resting on the mattress by selectively inflating or deflating one or more selected inflatable cells of the plurality of inflatable cells.

12. The system of claim 1, wherein the capacitive sensor comprises at least one capacitive cell including a flat condenser comprising at least one layer of a compressible dielectric insulating material interposed between two layers of conductive material.

13. A method for monitoring a patient on an air support system, the method comprising:

receiving, at a respiration signal processing module, the output of a capacitive sensor system having a capacitive sensor positioned at the underside of an air filled mattress; and at the signal processing module:

periodically sampling the capacitive sensor system output to obtain measurements of incremental body displacement;

analyzing a plurality of the samples to determine one or more values for parameters of patient respiratory rate; and determining when one or more of the parameter values indicate abnormal respiration;

wherein analyzing the plurality of the samples to determine one or more values for parameters of patient respiratory rate comprises:

performing a cycle counting technique on the plurality of samples to determine a first value indicative of respiratory rate;

separately performing analysis of a power spectrum of the plurality of samples to determine a frequency corresponding to a second value indicative of respiratory rate;

combining results of the cycle counting technique with results of the analysis of the power spectrum by averaging the first and second values to determine an output value indicative of patient respiratory rate;

analyzing the plurality of samples comprises determining a periodic variation in the output of the capacitive sensor system using a predetermined number of accumulated samples, and determining the patient respiratory rate based upon the periodic variation, the periodic variation in the output of the capacitive sensor system is determined using a moving sample window; and determining when one or more of the parameter values indicate abnormal respiration comprises comparing the patient respiratory rate with an upper and/or lower threshold value, wherein the patient respiratory rate passing beyond the upper and/or lower threshold value indicates abnormal respiration.

14. The method of claim 13, wherein analyzing the plurality of the samples to determine one or more values for parameters of patient respiratory rate involves use of a histogram function.

15. The system of claim 1, wherein analyzing the plurality of the samples to determine one or more values for parameters of patient respiratory rate involves use of a histogram function.

* * * * *